US008454570B2

(12) United States Patent
Carstens

(10) Patent No.: US 8,454,570 B2
(45) Date of Patent: *Jun. 4, 2013

(54) SYSTEM COMPRISING THONG-SHAPED HOLDER AND ABSORBENT ARTICLE

(75) Inventor: Jerry Edward Carstens, West Chester, OH (US)

(73) Assignee: RUSL, LLC, West Chester, OH (US)

( * ) Notice: Subject to any disclaimer, the term of this patent is extended or adjusted under 35 U.S.C. 154(b) by 321 days.

This patent is subject to a terminal disclaimer.

(21) Appl. No.: 12/977,749

(22) Filed: Dec. 23, 2010

(65) Prior Publication Data

US 2011/0092945 A1     Apr. 21, 2011

Related U.S. Application Data

(63) Continuation of application No. 11/135,034, filed on May 23, 2005, now Pat. No. 7,867,211.

(51) Int. Cl.
*A61F 13/15*  (2006.01)

(52) U.S. Cl.
USPC ........... 604/385.22; 604/385.26; 604/385.01; 604/396

(58) Field of Classification Search
USPC ............ 604/385.01, 385.22, 385.24, 385.26, 604/402, 400, 396
See application file for complete search history.

(56) References Cited

U.S. PATENT DOCUMENTS

| | | |
|---|---|---|
| 514,717 A | 2/1894 | Kirwin |
| 2,333,839 A | 12/1941 | Blackburn et al. |
| 2,792,698 A | 5/1957 | Hampp |
| 2,837,095 A | 6/1958 | Stevenson |
| 2,946,211 A | 7/1960 | Morancy |
| 3,098,369 A | 7/1963 | Burleson et al. |
| 3,368,563 A | 2/1968 | Scheier |
| 3,552,154 A | 1/1971 | Lesley |
| 3,578,546 A | 5/1971 | Morancy |
| 3,608,551 A | 9/1971 | Seijo |
| 3,910,075 A | 10/1975 | Holliday |
| 3,929,135 A | 12/1975 | Thompson |
| 4,057,061 A | 11/1977 | Ishikawa |
| 4,289,137 A | 9/1981 | Dell et al. |
| 4,324,245 A | 4/1982 | Mesek et al. |
| 4,342,314 A | 8/1982 | Radel et al. |
| 4,424,809 A | 1/1984 | Yovankin |
| 4,463,045 A | 7/1984 | Ahr et al. |
| 4,527,403 A | 7/1985 | Fullbright et al. |
| 4,589,876 A | 5/1986 | Van Tilburg |
| 4,687,478 A | 8/1987 | Van Tilburg |

(Continued)

OTHER PUBLICATIONS

Package for product: Kotex® Lightdays® Thong, Bar Code/SKU 036000012156, Kimberly-Clark, marketed prior to May 2004.

(Continued)

*Primary Examiner* — Jacqueline F. Stephens
(74) *Attorney, Agent, or Firm* — Hasse & Nesbitt LLC; Donald E. Hasse

(57) ABSTRACT

A system comprising a thong-shaped holder for holding an absorbent article in close bodily contact in the pudendal region of the wearer. The holder comprises a front region, a crotch region having a specified Crotch Holding Force, and a rear region. The crotch region of the holder typically is elastically extensible in both the longitudinal and lateral directions. The holder provides an upward holding force against the absorbent article in the crotch region to hold the article in close bodily contact. A method for holding such an article in close bodily contact by wearing the holder is also disclosed.

20 Claims, 14 Drawing Sheets

U.S. PATENT DOCUMENTS

| | | | |
|---|---|---|---|
| 4,695,278 A | 9/1987 | Lawson |
| 4,777,073 A | 10/1988 | Sheth |
| 4,813,950 A | 3/1989 | Branch |
| 4,846,824 A | 7/1989 | Lassen et al. |
| 4,917,697 A | 4/1990 | Osborn, III et al. |
| 4,935,287 A | 6/1990 | Johnson et al. |
| 4,950,264 A | 8/1990 | Osborn, III |
| 4,974,762 A | 12/1990 | Boretsky et al. |
| 4,990,147 A | 2/1991 | Freeland |
| 5,006,394 A | 4/1991 | Baird |
| 5,009,653 A | 4/1991 | Osborn, III |
| 5,207,663 A | 5/1993 | McQueen |
| 5,267,992 A | 12/1993 | Van Tilburg |
| 5,336,208 A | 8/1994 | Rosenbluth et al. |
| 5,354,400 A | 10/1994 | Lavash et al. |
| 5,382,245 A | 1/1995 | Thompson et al. |
| 5,383,869 A | 1/1995 | Osborn, III |
| 5,389,094 A | 2/1995 | Lavash et al. |
| 5,389,181 A | 2/1995 | Vukos et al. |
| 5,395,399 A | 3/1995 | Rosenwald |
| 5,415,650 A | 5/1995 | Sigl |
| 5,484,429 A | 1/1996 | Vukos et al. |
| 5,489,283 A | 2/1996 | Van Tilburg |
| 5,527,302 A | 6/1996 | Endres et al. |
| 5,528,775 A | 6/1996 | Marenda |
| 5,558,657 A | 9/1996 | Hammons et al. |
| 5,562,648 A | 10/1996 | Peterson |
| 5,575,786 A | 11/1996 | Osborn, III |
| 5,584,829 A | 12/1996 | Lavash et al. |
| 5,607,760 A | 3/1997 | Roe |
| 5,609,587 A | 3/1997 | Roe |
| 5,611,790 A | 3/1997 | Osborn, III et al. |
| 5,624,426 A | 4/1997 | Roe et al. |
| 5,650,223 A | 7/1997 | Weinberger et al. |
| 5,651,778 A | 7/1997 | Melius et al. |
| 5,658,269 A | 8/1997 | Osborn, III et al. |
| 5,671,615 A | 9/1997 | Kjaergaard et al. |
| 5,674,212 A | 10/1997 | Osborn, III et al. |
| 5,674,216 A | 10/1997 | Buell et al. |
| 5,676,652 A | 10/1997 | Hunter et al. |
| 5,683,373 A | 11/1997 | Darby |
| 5,683,375 A | 11/1997 | Osborn, III et al. |
| 5,690,627 A | 11/1997 | Clear et al. |
| 5,713,886 A | 2/1998 | Sturino |
| 5,729,835 A | 3/1998 | Williams |
| 5,782,819 A | 7/1998 | Tanzer et al. |
| 5,891,121 A | 4/1999 | Redwine et al. |
| 5,895,381 A | 4/1999 | Osborn, III |
| 5,904,710 A | 5/1999 | Davis et al. |
| 5,906,637 A | 5/1999 | Davis et al. |
| 5,921,975 A | 7/1999 | Suzuki et al. |
| 5,938,649 A | 8/1999 | Ducker et al. |
| 5,954,705 A | 9/1999 | Sawaki et al. |
| 6,004,893 A | 12/1999 | Van Tilburg |
| 6,102,937 A | 8/2000 | Cramer et al. |
| 6,120,485 A | 9/2000 | Gustafsson et al. |
| 6,149,934 A | 11/2000 | Krzysik et al. |
| 6,156,024 A | 12/2000 | Schulte et al. |
| 6,171,291 B1 | 1/2001 | Osborn, III et al. |
| 6,183,458 B1 | 2/2001 | Ahlstrand et al. |
| 6,206,867 B1 | 3/2001 | Osborn, III et al. |
| 6,232,250 B1 | 5/2001 | Palumbo et al. |
| 6,254,584 B1 | 7/2001 | Osborn, III et al. |
| 6,270,486 B1 | 8/2001 | Brown et al. |
| 6,287,169 B1 | 9/2001 | Willms et al. |
| 6,287,288 B1 | 9/2001 | Osborn, III et al. |
| 6,290,979 B1 | 9/2001 | Roe et al. |
| 6,316,688 B1 | 11/2001 | Hammons et al. |
| 6,346,097 B1 | 2/2002 | Blaney |
| 6,350,256 B1 | 2/2002 | Palumbo et al. |
| 6,350,258 B1 | 2/2002 | Markowiecki |
| D454,195 S | 3/2002 | Kitzinger et al. |
| 6,355,022 B1 | 3/2002 | Osborn, III et al. |
| 6,358,235 B1 | 3/2002 | Osborn, III et al. |
| 6,375,646 B1 | 4/2002 | Widlund et al. |
| 6,387,084 B1 | 5/2002 | VanGompel et al. |
| 6,393,621 B1 | 5/2002 | Redwine et al. |
| 6,398,770 B1 | 6/2002 | Drevik |
| 6,409,714 B2 | 6/2002 | Osborn, III et al. |
| 6,416,501 B2 | 7/2002 | Brown et al. |
| 6,440,111 B1 | 8/2002 | Berba et al. |
| 6,443,934 B1 | 9/2002 | Glaug et al. |
| 6,475,202 B1 | 11/2002 | Hirsch |
| 6,494,871 B1 | 12/2002 | Lariviere et al. |
| 6,497,690 B2 | 12/2002 | Haarer |
| 6,502,250 B2 | 1/2003 | Suga et al. |
| 6,508,794 B1 | 1/2003 | Palumbo et al. |
| 6,524,289 B1 | 2/2003 | Larsson et al. |
| 6,524,291 B1 | 2/2003 | Bjorklund et al. |
| 6,527,757 B1 | 3/2003 | Jackson |
| 6,539,555 B2 | 4/2003 | Suga et al. |
| 6,551,292 B1 | 4/2003 | D'Acchioli et al. |
| 6,554,812 B2 | 4/2003 | Drevik |
| 6,569,138 B2 | 5/2003 | Helmfridsson et al. |
| 6,570,053 B2 | 5/2003 | Roe et al. |
| 6,572,597 B1 | 6/2003 | Nash |
| 6,582,411 B1 | 6/2003 | Carstens et al. |
| 6,586,654 B2 | 7/2003 | Drevik |
| 6,595,977 B1 | 7/2003 | Luizzi, Jr. et al. |
| 6,602,233 B1 | 8/2003 | Palumbo et al. |
| 6,602,237 B2 | 8/2003 | Helmfridsson et al. |
| 6,605,071 B1 | 8/2003 | Gray et al. |
| 6,613,031 B2 | 9/2003 | Glasgow et al. |
| 6,613,034 B2 | 9/2003 | Nozaki et al. |
| 6,613,175 B1 | 9/2003 | Moscherosch et al. |
| 6,616,649 B1 | 9/2003 | Ismail |
| 6,626,883 B2 | 9/2003 | Wada et al. |
| 6,629,965 B2 | 10/2003 | Drevik et al. |
| 6,632,210 B1 | 10/2003 | Glasgow et al. |
| 6,632,974 B1 | 10/2003 | Suzuki et al. |
| 6,641,569 B1 | 11/2003 | Coles et al. |
| 6,695,827 B2 | 2/2004 | Chen et al. |
| 6,702,801 B2 | 3/2004 | VanGompel et al. |
| 6,710,223 B1 | 3/2004 | Van Rijswijck et al. |
| 6,713,660 B1 | 3/2004 | Roe et al. |
| 6,726,668 B2 | 4/2004 | Underhill et al. |
| 6,733,482 B1 | 5/2004 | Coles et al. |
| 6,740,069 B2 | 5/2004 | Drevik |
| 6,746,436 B1 | 6/2004 | Sierri et al. |
| 6,761,710 B2 | 7/2004 | D'Acchioli et al. |
| 6,773,424 B2 | 8/2004 | Heyrman et al. |
| 6,802,832 B2 | 10/2004 | Hansson et al. |
| 6,969,378 B1 | 11/2005 | Vukos et al. |
| 7,018,368 B2 | 3/2006 | VanGompel et al. |
| 7,056,411 B2 | 6/2006 | Desai et al. |
| 7,223,818 B2 | 5/2007 | Autran et al. |
| 7,273,476 B2 | 9/2007 | Mueller et al. |
| 7,458,961 B2 | 12/2008 | Carstens |
| 7,462,173 B2 | 12/2008 | Carstens |
| 7,481,801 B2 | 1/2009 | Carstens |
| 7,537,587 B2 | 5/2009 | Carstens |
| 7,614,399 B2 | 11/2009 | Carstens |
| 7,785,311 B2 | 8/2010 | Carstens |
| 7,789,867 B2 | 9/2010 | Carstens |
| 7,803,147 B2 | 9/2010 | Carstens |
| 7,846,145 B2 | 12/2010 | Carstens |
| 7,867,211 B2 | 1/2011 | Carstens |
| 7,930,770 B2 | 4/2011 | Suga et al. |
| 7,931,639 B2 | 4/2011 | Suga et al. |
| 8,099,794 B2 | 1/2012 | Carstens |
| 8,172,820 B2 | 5/2012 | Carstens |
| 8,262,638 B2 | 9/2012 | Carstens |
| 8,348,918 B2 | 1/2013 | Carstens |
| 2001/0025140 A1 | 9/2001 | Torok et al. |
| 2002/0065497 A1 | 5/2002 | Kolby-Falk |
| 2002/0107497 A1 | 8/2002 | Osborn, III et al. |
| 2002/0128622 A1 | 9/2002 | Carvalho et al. |
| 2003/0004484 A1 | 1/2003 | Hammons et al. |
| 2003/0083637 A1 | 5/2003 | Killeen et al. |
| 2003/0091969 A1 | 5/2003 | Supinski et al. |
| 2003/0097109 A1 | 5/2003 | Bruce et al. |
| 2003/0153890 A1 | 8/2003 | Rosenfeld |
| 2003/0181884 A1 | 9/2003 | Carstens et al. |
| 2003/0208177 A1 | 11/2003 | D'Alessio et al. |
| 2003/0220622 A1 | 11/2003 | Hermansson et al. |
| 2003/0229327 A1 | 12/2003 | Imsangjan et al. |
| 2003/0229933 A1 | 12/2003 | Nelson |

| | | |
|---|---|---|
| 2004/0060649 A1 | 4/2004 | Van Gompel et al. |
| 2004/0092898 A1 | 5/2004 | Schafer et al. |
| 2004/0102747 A1 | 5/2004 | Bell et al. |
| 2004/0127881 A1 | 7/2004 | Stevens et al. |
| 2004/0193133 A1 | 9/2004 | Desai et al. |
| 2005/0090795 A1 | 4/2005 | Coleman |
| 2005/0096623 A1 | 5/2005 | Nhan et al. |
| 2005/0256489 A1 | 11/2005 | Sawyer et al. |
| 2006/0004341 A1 | 1/2006 | Olson et al. |
| 2006/0004342 A1 | 1/2006 | Sawyer et al. |
| 2006/0253093 A1 | 11/2006 | Beck et al. |
| 2006/0264865 A1 | 11/2006 | Carstens |
| 2006/0264867 A1 | 11/2006 | Carstens |
| 2006/0264868 A1 | 11/2006 | Carstens |
| 2006/0264869 A1 | 11/2006 | Carstens |
| 2006/0264870 A1 | 11/2006 | Carstens |
| 2006/0264871 A1 | 11/2006 | Carstens |
| 2006/0264872 A1 | 11/2006 | Carstens |
| 2006/0264873 A1 | 11/2006 | Carstens |
| 2006/0264874 A1 | 11/2006 | Carstens |
| 2006/0264877 A1 | 11/2006 | Carstens |
| 2006/0264878 A1 | 11/2006 | Carstens |
| 2006/0264879 A1 | 11/2006 | Carstens |
| 2006/0264880 A1 | 11/2006 | Carstens |
| 2006/0264881 A1 | 11/2006 | Carstens |
| 2006/0264882 A1 | 11/2006 | Carstens |
| 2006/0264883 A1 | 11/2006 | Carstens |
| 2006/0264884 A1 | 11/2006 | Carstens |
| 2007/0093771 A1 | 4/2007 | Aritzi et al. |
| 2007/0102461 A1 | 5/2007 | Carstens |
| 2007/0106237 A1 | 5/2007 | Carstens |
| 2007/0106350 A1 | 5/2007 | Carstens |
| 2007/0106352 A1 | 5/2007 | Carstens |
| 2007/0106353 A1 | 5/2007 | Carstens |
| 2007/0106354 A1 | 5/2007 | Carstens |
| 2007/0106355 A1 | 5/2007 | Carstens |
| 2007/0106356 A1 | 5/2007 | Carstens |
| 2007/0142816 A1 | 6/2007 | Carstens |
| 2007/0287348 A1 | 12/2007 | Autran et al. |
| 2008/0119815 A1 | 5/2008 | Carstens |
| 2009/0030392 A1 | 1/2009 | Kanai et al. |
| 2010/0094240 A9 | 4/2010 | Desai et al. |
| 2010/0324522 A1 | 12/2010 | Carstens |
| 2010/0324525 A1 | 12/2010 | Carstens |
| 2010/0324526 A1 | 12/2010 | Carstens |
| 2011/0092945 A1 | 4/2011 | Carstens |

OTHER PUBLICATIONS

Package for product: Carefree® Thong, Bar Code/SKU 380041261005, Johnson & Johnson, marketed prior to May 2004, (2 pages).

Package for product: Always®, Pantiliners, Thong|Mini-Slip, Bar Code/SKU 037000347590, The Procter & Gamble Company, marketed prior to May 2004, (2 pages).

Package for product: Stayfree® Thong Maxi, Bar Code/SKU 38004-0995000, Johnson & Johnson, marketed prior to May 2004, (2 pages).

Internet: Calvin Klein Tailored Stretch Thong, ASIN: B0001MIU22, amazon.com—Apparel & Accessories, dated Aug. 26, 2004.

Internet: Champion Women's Seamless Sport Panties, Style CH4613G, dated Aug. 26, 2004.

Internet: Barelythere Microfiber Thong Panty, Style 2670, amazon.com—Apparel & Accessories, dated Aug. 25, 2004.

Internet: OnGossamer Mesh Thong Panty, Style 3212, amazon.com—Apparel & Accessories, dated Aug. 26, 2004.

Internet: Body Wrap 44840 Thong, HerRoom.com, dated Aug. 25, 2004.

Internet: DKNY Cotton Lycra Thong Panty, Style 445010, amazon.com—Apparel & Accessories, dated Aug. 26, 2004.

SYSTEM COMPRISING THONG-SHAPED HOLDER AND ABSORBENT ARTICLE

CROSS-REFERENCE TO RELATED APPLICATION

This application is a continuation of U.S. patent application Ser. No. 11/135,034, filed on May 23, 2005 now U.S. Pat. No. 7,867,211, incorporated herein by reference.

FIELD OF THE INVENTION

The present invention relates to a thong-shaped holder for holding an article in close bodily contact in the pudendal region of the wearer. More particularly, the invention relates to such a holder for an article having a compatible shape and size, such as a thong sanitary pad or urinary incontinence pad. The invention also relates to a system comprising the thong-shaped holder and an article for use therewith, and a method for holding such an article in close bodily contact by wearing the holder.

BACKGROUND OF THE INVENTION

Disposable absorbent articles are commercially available in a wide variety of configurations for absorbing and retaining urine, menstrual fluids and other vaginal discharges. Unfortunately, such articles may leak along their periphery due to poor fit or improper placement. Such leakage frequently results in soiling of a wearer's undergarments, clothing or bedding.

To provide additional protection against leakage, it is known to use a washable and reusable garment, such as a menstrual short or panty, in combination with a disposable absorbent pad. U.S. Pat. No. 4,813,950, Branch, discloses a washable menstrual panty having an outer lining of spandex, soft tricot, etc. that provides a "skin tight or almost skin tight" fit. Similarly, existing Japanese-style menstrual shorts act like a girdle or a tight fitting panty that attempts to hold an absorbent article in the wearer's pudendal region. However, the tight fit of such undergarments has been reported to be uncomfortable to wearers, and there is no apparent provision for directly lifting an absorbent article to a position close to a wearer's pudendal area.

A menstrual short panty having an elastic piece fixed to the front and rear of the crotch region in an elongated state is described in U.S. Pat. No. 3,608,551, Seijo. The elastic piece is said to keep a sanitary pad raised and in contact with the body irrespective of physical movements. While such a device may improve pad-to-body contact along a centerline of a wearer's body, the device is unlikely to lift an absorbent pad into conformity with the external surface of a wearer's labia. Further, the narrow central elastic piece may cause the device to be uncomfortable to wearers because all of the lifting force appears to be concentrated along the centerline.

U.S. Pat. No. 6,393,621, Redwine et al., discloses undergarments having a crotch region with a longitudinal stretch control member and a plurality of angled stretch control members that limit stretch in the longitudinal and lateral directions and cause the crotch region to conform to the wearer's skin. The rear region has a lifting member the cooperates with the rear region, the front region and the longitudinal stretch control member to provide a "z-direction" biasing force that causes the crotch region and an absorbent article disposed thereon to be lifted into close bodily contact when the undergarment is worn. Such undergarments provide improved fit and performance, but can still result in undesirable leakage during use.

PCT Application WO 99/25289 describes a system comprising an undergarment for supporting an absorbent article in sustained close contact with a wearer's body. The absorbent article is said to be flexible under the body-contacting forces that are applied by the supporting garment so that it conforms to the wearer's body.

While the above patents and applications disclose various undergarments for holding absorbent articles against the body, there is a continuing need for a holder capable of holding an absorbent article in close bodily contact in the pudendal region to provide improved leakage protection and wearer comfort.

SUMMARY OF THE INVENTION

The present invention relates to a system comprising:
a) a thong-shaped holder for holding an absorbent article in close bodily contact in the pudendal region, said holder having a longitudinal centerline defining a longitudinal direction and a lateral centerline defining a lateral direction, said holder comprising:
  1) a front region;
  2) a crotch region attached to the front region, said crotch region having a Crotch Holding Force (CHF-4.0) of greater than about 0.1 kgf and a Crotch Holding Force (CHF-5.5) of less than about 1.0 kgf; and
  3) a rear region attached to the front and crotch regions and cooperating with the front region to provide an adjustable waistband; and
b) an absorbent article capable of being held in close bodily contact in the pudendal region by said thong-shaped holder, said absorbent article comprising a liquid pervious side, a liquid impervious side opposite the liquid pervious side, and an absorbent component between the liquid pervious side and the liquid impervious side, wherein the liquid pervious side and the liquid impervious side are arranged to form a unitary structure.

The invention also relates to a system comprising:
a) a thong-shaped holder for holding an absorbent article in close bodily contact in the pudendal region, said holder having a longitudinal centerline defining a longitudinal direction and a lateral centerline defining a lateral direction, said holder comprising:
  1) a front region;
  2) a crotch region attached to the front region, said crotch region having a Crotch Holding Force (CHF-4.0) of greater than about 0.1 kgf and a Crotch Holding Force (CHF-5.5) of less than about 1.0 kgf;
  3) a rear region attached to the front and crotch regions and cooperating with the front region to provide an adjustable waistband; and
  4) side elastics in the crotch region; and
b) an absorbent article capable of being held in close bodily contact in the pudendal region by said thong-shaped holder, said absorbent article comprising a liquid pervious side, a liquid impervious side opposite the liquid pervious side, and an absorbent component between the liquid pervious side and the liquid impervious side, wherein the liquid pervious side and the liquid impervious side are arranged to form a unitary structure, said absorbent article comprising a primary absorbent core that has a thong shape and a width that is less than or equal to the width of the crotch region of the holder, and comprising wings having a length at least about 75% of the length of the absorbent article.

In another aspect, the invention relates to a system comprising:
a) a thong-shaped holder for holding an absorbent article in close bodily contact in the pudendal region, said holder having a longitudinal centerline defining a longitudinal direction and a lateral centerline defining a lateral direction, said holder comprising:
 1) a front region;
 2) a crotch region attached to the front region, said crotch region having a Crotch Holding Force (CHF-4.0) of greater than about 0.1 kgf and a Crotch Holding Force (CHF-5.5) of less than about 1.0 kgf;
 3) a rear region attached to the front and crotch regions and cooperating with the front region to provide an adjustable waistband; and
 4) side elastics in the crotch region, said side elastics having an Elastic Holding Force (EHF-4.5) of less than about 1.0 kgf; and
b) an absorbent article capable of being held in close bodily contact in the pudendal region by said thong-shaped holder, said absorbent article comprising a liquid pervious side, a liquid impervious side opposite the liquid pervious side, and an absorbent component between the liquid pervious side and the liquid impervious side, wherein the liquid pervious side and the liquid impervious side are arranged to form a unitary structure.

DETAILED DESCRIPTION OF THE INVENTION

Figure 1:
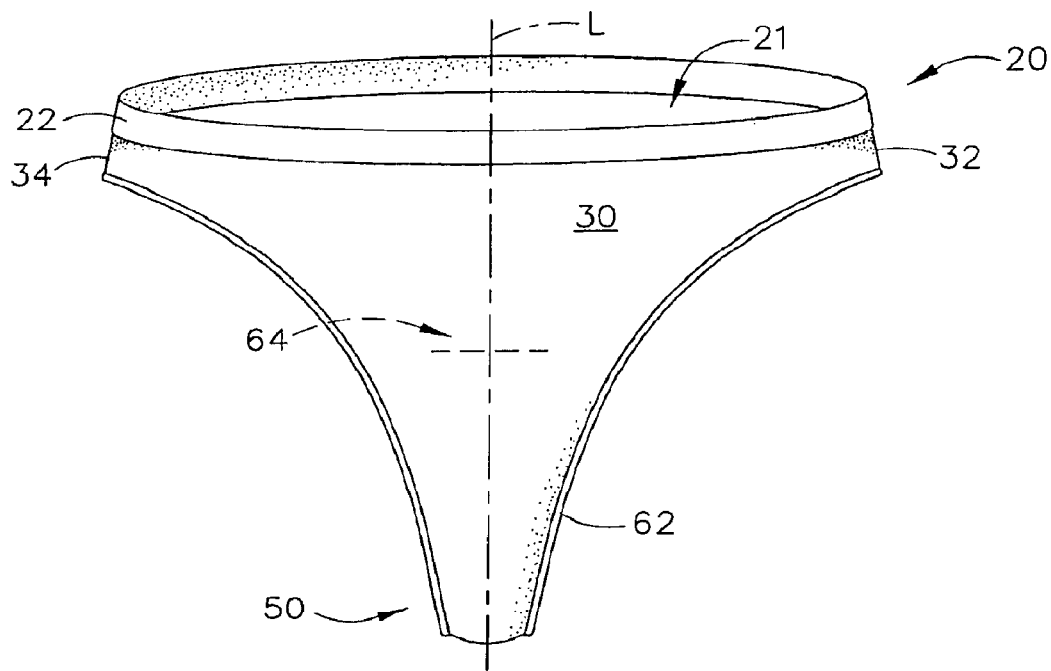
FIG. 1 is a front view of a thong-shaped holder of the invention.

The thong-shaped holder of the invention is suitable for holding a compatible article, typically an absorbent article, in close bodily contact in the pudendal region of the wearer. In one embodiment, the holder is intended for use with menstrual articles such as sanitary pads, interlabial devices, pantiliners, and the like. In another embodiment, the holder is intended for use with urinary incontinence articles, such as pads, diaper inserts, and the like. In still another embodiment, the holder is intended for use with a disposable fluid management device comprising a bag, such as a menstrual or urine fluid management device. The holder may also be used with an article comprising a lotion coating, a skin care composition, or a therapeutic composition that is partially transferable to the wearer's skin, or a sensor operatively connected to the article. The absorbent or other article herein typically has a compatible shape and size so that it fits within the low-motion zone of the wearer and avoids significant leg movement interactions that can interfere with close bodily contact in the pudendal region.

While not intending to be limited by theory, it is believed that the holder provides an upward holding force against the article in the crotch region to hold the article in close bodily contact when the holder is worn. The thong shape of the holder keeps the article in the low-motion zone between the legs of the wearer and avoids significant leg movement interactions often encountered with conventional brief-style undergarments and conventional pads. The thong-shaped holder thus holds the article in close bodily contact throughout a range of wearer motions, often providing improved performance (e.g., less leakage from the absorbent article and/or less soiling of clothing). Additionally, when the holder and article are designed and coordinated to work together, the resulting system can be optimized to provide consumer benefits such as leakage prevention, wearing comfort, stay-in-place performance, correct placement, discreetness, and/or cost effectiveness.

The invention also relates to a system comprising the thong-shaped holder and a compatible article, and a method for holding such an article in close bodily contact in the pudendal region by wearing the holder. The article typically is an absorbent article comprising a liquid pervious side, a liquid impervious side opposite the liquid pervious side, and an absorbent component between the liquid pervious side and the liquid impervious side. The liquid pervious side and the liquid impervious side of the article are arranged to form a unitary structure. The article has a compatible size and shape, and is capable of being held in close bodily contact in the pudendal region by the holder. Compatible absorbent articles include sanitary and incontinent pads, interlabial inserts, pantiliners, and fluid collection bags and other devices. Typically, the article and the holder are designed and coordinated to work together and provide improved performance, comfort and/or fit of the article.

The system of the invention comprises at least one article in combination with the thong-shaped holder. The article/holder system can be used with or without the wearer's normal underwear or panty. For additional protection against leakage of bodily fluids, the wearer may use the absorbent article/holder system of this invention in combination with at least one additional absorbent article, such as a conventional sanitary pad or pantiliner worn in the wearer's normal underwear, a tampon, an interlabial pad, or a disposable fluid management device comprising a bag. The article and holder of this system may be packaged in a common, bundled, coordinated, or associated package or packages, and may be sold as a kit, for example a feminine hygiene kit.

As used herein, the term "absorbent article" refers to articles that are placed against or in proximity to the body in the wearer's pudendal/perineum region to acquire, absorb, and contain the various exudates discharged from the body. The term "absorbent article" is intended to include sanitary pads, pantiliners, interlabial devices, incontinence pads, fluid collection bags and other devices, and other articles worn in the crotch region.

The term "sanitary pad" refers to an article worn adjacent to the pudendal region that is intended to absorb and contain the various exudates that are discharged from the body (e. g., blood, menses, and urine).

The term "disposable" refers to structures that are intended to be discarded after a single use or a few uses (i.e., they are not intended to be cleaned, laundered or otherwise restored and/or reused after use). Such structures may be recycled, composted or otherwise disposed of in an environmentally compatible manner. While the articles described herein are typically disposable, they may be designed to be cleaned, laundered, restored and/or reused many times.

The term "pudendal region" refers to the external genitalia region, especially for a female, including the labia majora, the labia minora, the clitoris and the vaginal vestibule.

The term "perineum" refers to the external region of the body between the anus and the pudendal region.

The term "vaginal introitus" refers to the entrance or opening to the vagina

The term "gluteal groove" refers to the crevice between the buttocks (gluteus maximi) extending upwardly from the perineum.

The terms "fluid", "liquid" and the like are intended to be interchangeable and refer to materials that are in a liquid state at a temperature of about 38° C.

As noted above, the invention provides a holder that holds an article, particularly an absorbent article, against a wearer's body in the pudendal region. With a conventional undergarment, the crotch region typically does not hold and maintain the article in close bodily contact. For example, the article may sag when the wearer's legs arc brought together. Even conventional thong undergarments typically just cover the pudendal region and do not provide sufficient upward holding force to hold and maintain an absorbent article in close contact with the body. On the other hand, the holder of the invention holds the article substantially against the pudendal region, i.e., in the low-motion zone where there is little or no interference caused by leg movements. The holder typically maintains the upward force against the article throughout a range of body motions so that the article is held in close bodily contact. The close bodily contact and the reduction in relative motion between the article and the pudendal region generally result in improved performance (e.g., less leakage and/or less soiling of clothing). Moreover, the holder is comfortable to wear notwithstanding the close conformity of the holder and article to the wearer's body. It is believed that the sufficient and comfortable upward holding force provided by the crotch region of the holder against the article is due at least in part to the force exerted radially and axially by the stretch material used. The crotch region can be characterized as having a relatively low Crotch Holding Force value at a given extension distance, when measured as described herein. In contrast, conventional undergarments have often attempted to conform an absorbent article to the pudendal area by using stretch materials of relatively high stretch modulus, often configured as elasticized lifting members (e.g., cinches) or by a very tight overall fit with high contractive forces, such as seen with Japanese menstrual shorts. Undergarments of these types generally have high holding force values at a given extension distance, and are often described as uncomfortable.

Figure 2:
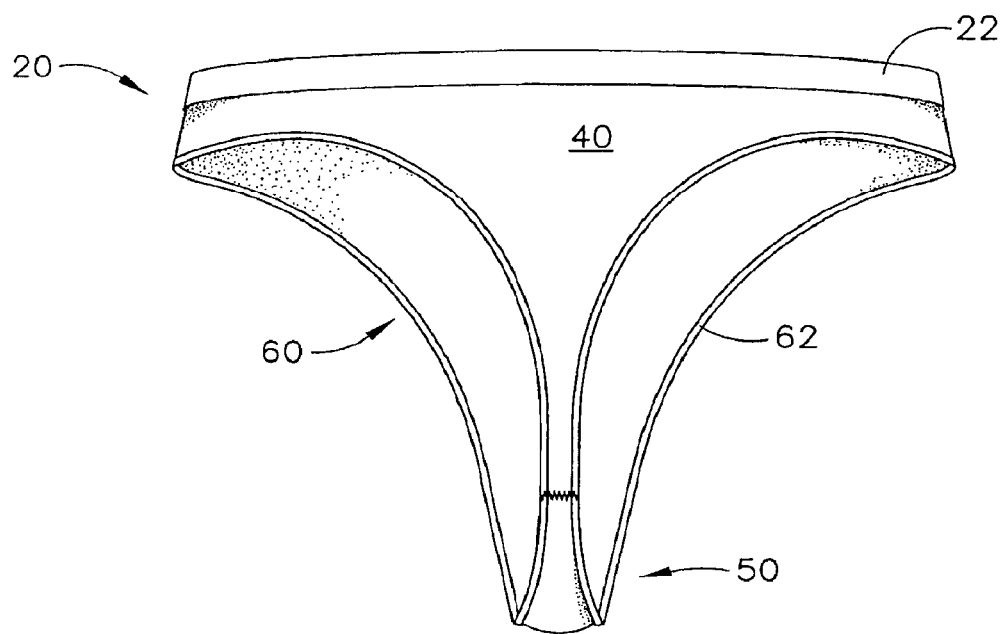
FIG. 2 is a rear view of the holder shown in FIG. 1.

While the present invention encompasses a wide variety of holder designs and compatible articles, it will often be described in terms of a thong-shaped holder comprising a material of relatively high stretch and low stretch modulus, used in conjunction with an absorbent article such as a sanitary pad. FIGS. 1 and 2 show front and rear views of such a holder of the invention. The holder comprises a front region 30, a crotch region 50 attached to the front region, and a rear region 40 attached to the front and crotch regions. The front and rear regions cooperate to provide an adjustable waistband, such as elasticized waistband 22. The holder is thus provided with a waist opening 21 that allows entry into the holder. The front, crotch and rear regions cooperate to provide a pair of leg openings 60. The crotch region extends between the front region and the rear region and to side elastics 62 attached to the leg openings. In one embodiment, the front, rear, and crotch regions are elastic in the lateral and longitudinal directions.

Figure 3:
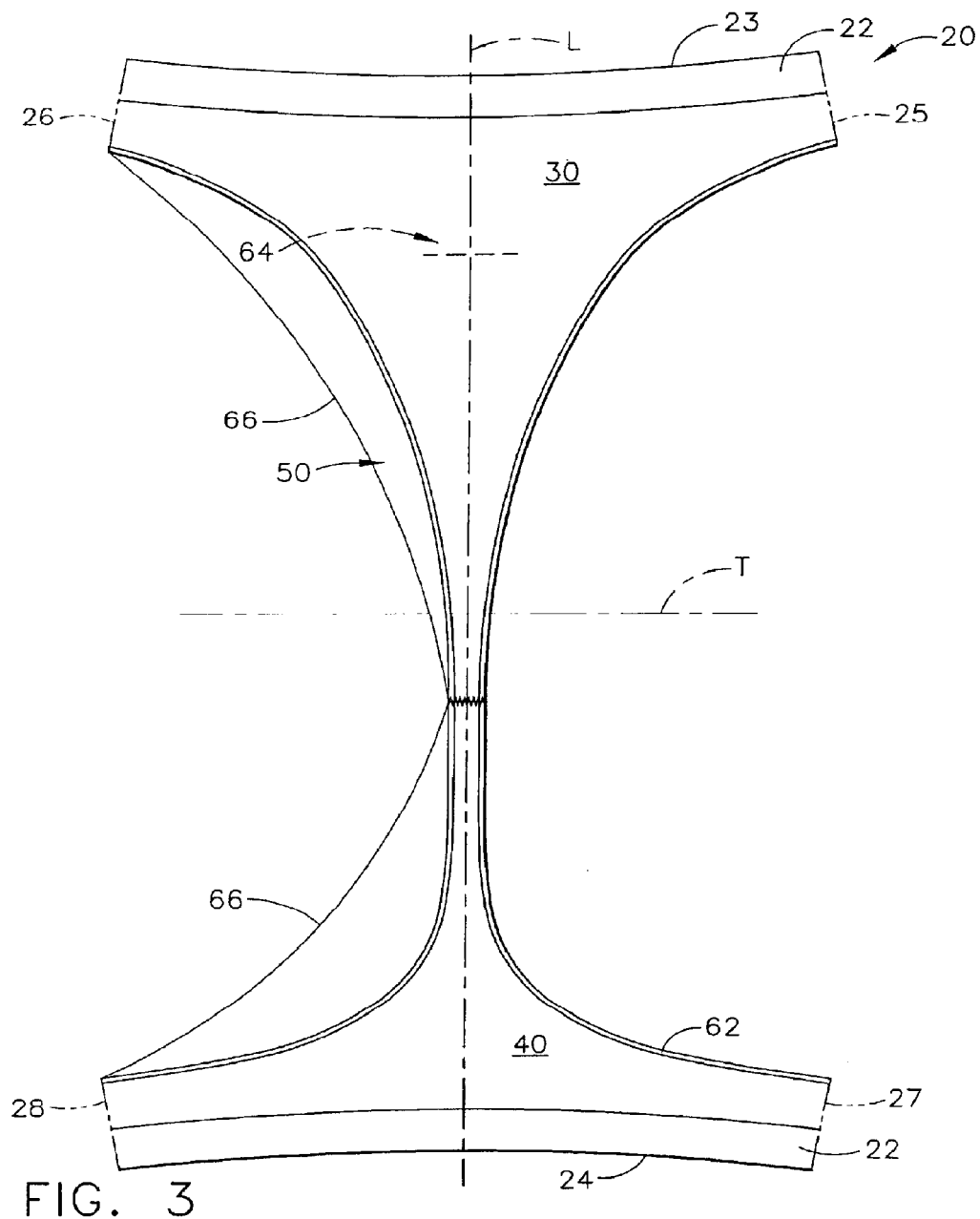
FIG. 3 is a plan view of the holder of FIG. 1 that has been opened at the sides, with the elastic components pulled flat, and further comprising an extension or panel on one side of the holder.

FIG. 3 shows the holder 20 in a full flat out position wherein each of the sides 32 and 34 has been opened and elastic components have been pulled flat. FIG. 3 can also be considered to be a plan view of the holder. The holder has a longitudinal centerline L and a lateral centerline T. The term "longitudinal" refers to a line, axis or direction in the plane of the holder that is generally aligned with (e. g., approximately parallel to) a vertical plane that bisects a standing wearer into left and right body halves when the holder is worn. The term "lateral" refers to a line, axis or direction that lies within the plane of the holder that is generally perpendicular to the longitudinal direction. The holder typically is symmetric about the longitudinal centerline L and asymmetric about the lateral centerline T.

The holder 20 can comprise woven, nonwoven (with stretch incorporated as known in the art) or knit fabrics, but typically comprises a knit fabric. Other materials having the requisite mechanical properties are also suitable. The holder may be durable or disposable, but typically is disposed of after a period of time (e.g., about 3 to 9 months) when it begins to lose elasticity or otherwise shows wear. When the holder is a knit fabric, the mechanical properties of the various components can be provided by a combination of the knit pattern used for a particular component and the yarns that are used. In one embodiment, the stretch properties of the crotch region of the holder are derived from circular knit materials known in the art. In one embodiment, the front region, the crotch region, and the rear region are wholly knit. The holder typically comprises material having a basis weight greater than that of hosiery and less than conventional undergarments in order to provide a desired "sheerness". This low basis weight and sheerness facilitates the holder being worn comfortably under normal underwear, or in place of normal underwear.

As shown in FIGS. 1 and 2, the front region 30 is that portion of holder 20 that cooperates with the rear region 40 to encircle a wearer's waist and hips. The front region cooperates with the rear region to define a waist opening 21 that allows entry into the holder, and to provide an adjustable waistband such that the waist opening conforms to a wearer's waist. The adjustable waistband may be an adjustable string, tie or belt, but typically is an elasticized waistband, such as elasticized waistband 22. The elasticized waistband may be formed by providing an elastic member, such as Lycra® or spandex material, adjacent each distal end of the blank shown in FIG. 3. The elasticized waistband typically comprises the same yarn as, and is integrally knit with, the front region and the rear region. More typically, the elasticized waistband comprises a turned welt as known in the art. One knitting pattern for the elasticized waistband comprises a combination of plain knit stitches and float stitches wherein every fourth wale is provided with a positive float stitch. The front, rear, and crotch regions also cooperate to define the leg openings 60, as shown in FIG. 1.

The front region 30 can be cut to an appropriate shape from a woven or nonwoven material and joined to the remaining portions of the holder 20, but is typically wholly plain knit, more typically jersey knit, from a combination of elastically extensible and non-elastically extensible yarns. The elastic properties of the individual yarns and the particular knitting pattern can be used to define the mechanical properties of the front region. In one embodiment, the front region comprises wholly plain knit, e.g., jersey knit, using Lycra® or spandex yarn having suitable mechanical properties in all courses. Other knitting patterns and alternative yarns can be used to provide the desired mechanical properties.

While the front region 30 need not comprise elastic material, it is typically extensible in both the longitudinal and lateral directions. Such elastic extensibility enables the holder 20 to fit a variety of bodily shapes and sizes and provides good conformity to a wearer's body. An extensible front region further cooperates with the rear region 40 and the crotch region 50 to provide an upward holding force within the crotch region of the holder throughout a wide range of wearer movements. The upward holding force helps maintain an article, such as sanitary pad 200 shown in FIG. 5, worn with the holder in close bodily contact in the wearer's pudendal region. The upward force directs the sanitary pad 200 such that it is held closely against the wearer's body, wherein the front edge 202 of the pad lies in a position anterior to the introitus and the rear edge 204 lies posterior to the introitus. The upward force also helps maintain the sanitary pad in position throughout a wide range of wearer motions.

The crotch region 50 is positioned along the longitudinal centerline L of holder 20 between the front region 30 and the rear region 40. The crotch region cooperates with the front region and the rear region to define the leg openings 60. The crotch region is that portion of the holder that supports the article, such as sanitary pad 200, and holds it in close bodily contact in the wearer's pudendal area. The crotch region has a generally trapezoidal shape. When measured in a flat and non-extended state, the crotch region has a width measured 10.0 cm above the lateral centerline of from about 6.0 to about 15.0 cm, and a width at the lateral centerline of from about 1.5 to about 10.0 cm. Typically, the crotch region has a width measured 10.0 cm above the lateral centerline of from about 8.0 to about 12.0 cm, and a width at the lateral centerline of from about 2.5 to about 8.0 cm. In one embodiment, the crotch region has a width measured 10.0 cm above the lateral centerline of from about 9.0 to about 11.0 cm, and a width at the lateral centerline of from about 4.0 to about 5.0 cm. When used with an absorbent article in a system of the invention, the crotch region width typically is greater than or equal to the width of the primary absorbent core.

The crotch region 50 cooperates with the front region 30 and the rear region 40 so that the holder 20 as worn provides a comfortable but sufficient upward holding force against the article. Without being bound by theory, it is believed that the upward holding force provided by the crotch region against the article is due at least in part to the compressive holding force provided by the stretch material therein. When the crotch region is stretched in use, the material exerts compressive forces against the article so as to hold it closely against the wearer's pudendal area. This conformity is maintained over a wide range of body movement, e.g., close pad-to-body contact is maintained when a wearer's legs are close together, spread apart, and/or moving front to back during walking. The holding force is great enough to securely hold the article against the body, but not great enough to cause wearer discomfort or to push the article out of position, especially during body movement. The crotch material typically has relatively low stretch modulus and provides relatively high "available stretch" as worn. This high available stretch in both the lateral and longitudinal directions, combined with sufficient but relatively low holding force, helps to maintain the article in close bodily contact across a range of body sizes, article (e.g., pad) sizes, and body motions. The crotch region of the holder has a Crotch Holding Force (CHF-4.0) of greater than about 0.1 kgf, typically greater than about 0.2 kgf, as measured by the Crotch Holding Force method presented herein. In one embodiment, the crotch region has a Crotch Holding Force (CHF-5.5) of greater than about 0.2 kgf, typically greater than about 0.3 kgf. The crotch region also has a Crotch Holding Force (CHF-2.0) of less than about 1.0 kgf, typically less than about 0.8 kgf, more typically less than about 0.6 kgf. In one embodiment, the crotch region has a Crotch Holding Force (CHF-4.0) of less than about 1.0 kgf, typically less than about 0.8 kgf, more typically less than about 0.6 kgf. In another embodiment, the crotch region has a Crotch Holding Force (CHF-5.5) of less than about 1.0 kgf, typically less than about 0.8 kgf. In yet another embodiment, the crotch region has a Crotch Holding Force (CHF-6.5) of less than about 1.4 kgf, typically less than about 1.2 kgf.

The crotch region 50 can comprise any woven material, nonwoven material (with stretch incorporated as known in the art), knit material, or the like that possesses the requisite physical properties. Similarly, the crotch region can comprise one material or a combination of materials, stitching, and/or design patterns that collectively possess the requisite physical properties. The crotch region can be cut to an appropriate shape and size, and joined to the remaining portions of the holder. The crotch region is typically wholly plain knit, more typically jersey knit, from a combination of elastically extensible and non-elastically extensible yarns. The elastic properties of the individual yarns and the particular knitting pattern can be used to define the mechanical properties of the crotch region. In one embodiment, the crotch region comprises wholly plain knit, e.g., jersey knit, using elastomeric fiber material such as Lycra® or spandex yarn having suitable mechanical properties in all courses. Other knitting patterns and alternative yarns can be used to provide the desired mechanical properties. Typically the crotch region comprises a knit material having a Crotch Holding Force similar to that of the material used to construct the front region 30 and/or the rear region 40. More typically, the crotch region is integrally knit with the front region and/or the rear region using a plain knit pattern. Suitable yarns include natural yarns, such as cotton yarns and wool yarns, and synthetic yarns, such as nylon yarns, polyester yarns, acrylic yarns, and combinations thereof, e.g., nylon yarns and cotton yarns. Typically, elastomeric fiber material such as Lycra® or spandex yarns are used with these natural and/or synthetic fibers to provide the desired stretch properties.

The rear region of the holder cooperates with the front region to provide an adjustable, e.g., an elasticized, waistband. The rear region typically has a width measured 5.0 cm above the lateral centerline of from about 0.5 to about 5.0 cm, more typically from about 2.0 to about 3.0 cm. This portion of the rear region typically fits in the gluteal grove and provides a "z-direction" biasing force in the perineum area when the holder is worn.

The rear region 40 cooperates with the front region 30 to encircle a wearer's waist and hips. As shown in FIG. 2, the rear region in the thong-shaped holder typically does not cover a wearer's buttocks, and often comprises a relatively narrow strap, band or string that extends up the gluteal grove. In one embodiment, the width of the strap, band or string is from about 0.5 cm to about 5.0 cm, measured 5.0 cm above the lateral centerline. The rear region typically widens above the buttocks in the region near the waistband, as with conventional thong-shaped undergarments.

As described above regarding the front region 30, the rear region 40 may comprise a woven or nonwoven material, but typically comprises wholly plain knit, e.g., jersey knit, from a combination of elastically extensible and non-elastically extensible yarns. The elastic properties of the individual yarns and the particular knitting pattern can be chosen to define suitable mechanical properties. In one embodiment, the rear region comprises wholly plain knit, such as jersey knit, using Lycra® or spandex yarn having suitable mechanical properties in all courses. Other knitting patterns and alternative yarns can be used to provide the desired mechanical properties.

While the rear region 40 need not comprise an elastic material, it is typically extensible in both the longitudinal and lateral directions, particularly in portions of the rear region above the gluteal grove. Such elastic extensibility enables the holder 20 to fit a variety of bodily shapes and sizes and provides good conformity to a wearer's body. The extensible rear region further cooperates with the front and crotch regions to provide an upward holding force within the crotch region throughout a range of wearer movements. Such an upward force helps maintain an article (such as sanitary pad 200 shown in FIG. 5) worn with the holder in close bodily contact in the wearer's pudendal region. The rear region typically comprises material having a Crotch Holding Force in the range described above for the crotch region. The front, crotch, and rear regions are often comprised of the same material.

The front, crotch, and/or rear regions of the holder may comprise at least one additional extension or panel extending beyond these regions so long as it does not significantly interfere with the function of the holder. For example, the rear region may comprise one or more additional extensions or panels extending partially or fully over the buttocks that do not significantly interfere with the function of the holder. FIG. 3 illustrates the addition of an extension 66 to the front, crotch and rear regions of the holder 20. (The extension 66 is shown on only one side of holder 20, but when present it typically would be on both sides of the holder.) If such extensions are added, additional side elastics such as elastics 62 may be attached to the periphery of the extensions, or the side elastics may be omitted.

As can be seen in FIG. 1, the holder 20 of the invention is provided with a pair of leg openings 60. The front region 30, the rear region 40, and the crotch region 50 cooperate to define the periphery of each leg opening 60. This periphery typically is provided with side elastic 62 for elasticization of the leg opening. The side elastics 62 provide contractive forces around the periphery of the leg opening 60 contributing to the fit of the holder. The contractive forces should be great enough to fit comfortably against the body and help hold the article, and particularly any wings on the article, in contact with the body through the range of body motions. The contractive forces should not be so great as to cause discomfort to a wearer or adversely affect the holding properties of the crotch region. Typically, the side elastics have a relatively low stretch modulus and provide relatively high available stretch as worn. Such side elastics cooperate with the crotch region to provide a sufficient, comfortable and relatively uniform upward holding force against an article to hold it closely against a wearer's pudendal area. Since the side elastics in the crotch region of the holder typically fit in the wearer's low-motion zone and not around the legs, and the side elastics typically have high available stretch, leg movements do not significantly interfere with the close body fit of the article.

In one embodiment, the side elastics in the crotch region of the holder have an Elastic Holding Force (EHF-4.5) of less than about 1.0 kgf, typically less than about 0.8 kgf, more typically less than about 0.5 kgf, as measured by the Elastic Holding Force method presented herein. In another embodiment, the side elastics have an Elastic Holding Force (EHF-5.5) of less than about 1.0 kgf, typically less than about 0.8 kgf. The side elastics often have an Elastic Holding Force (EHF-4.5) of greater than about 0.1 kgf, typically greater than about 0.2 kgf.

Figure 4:
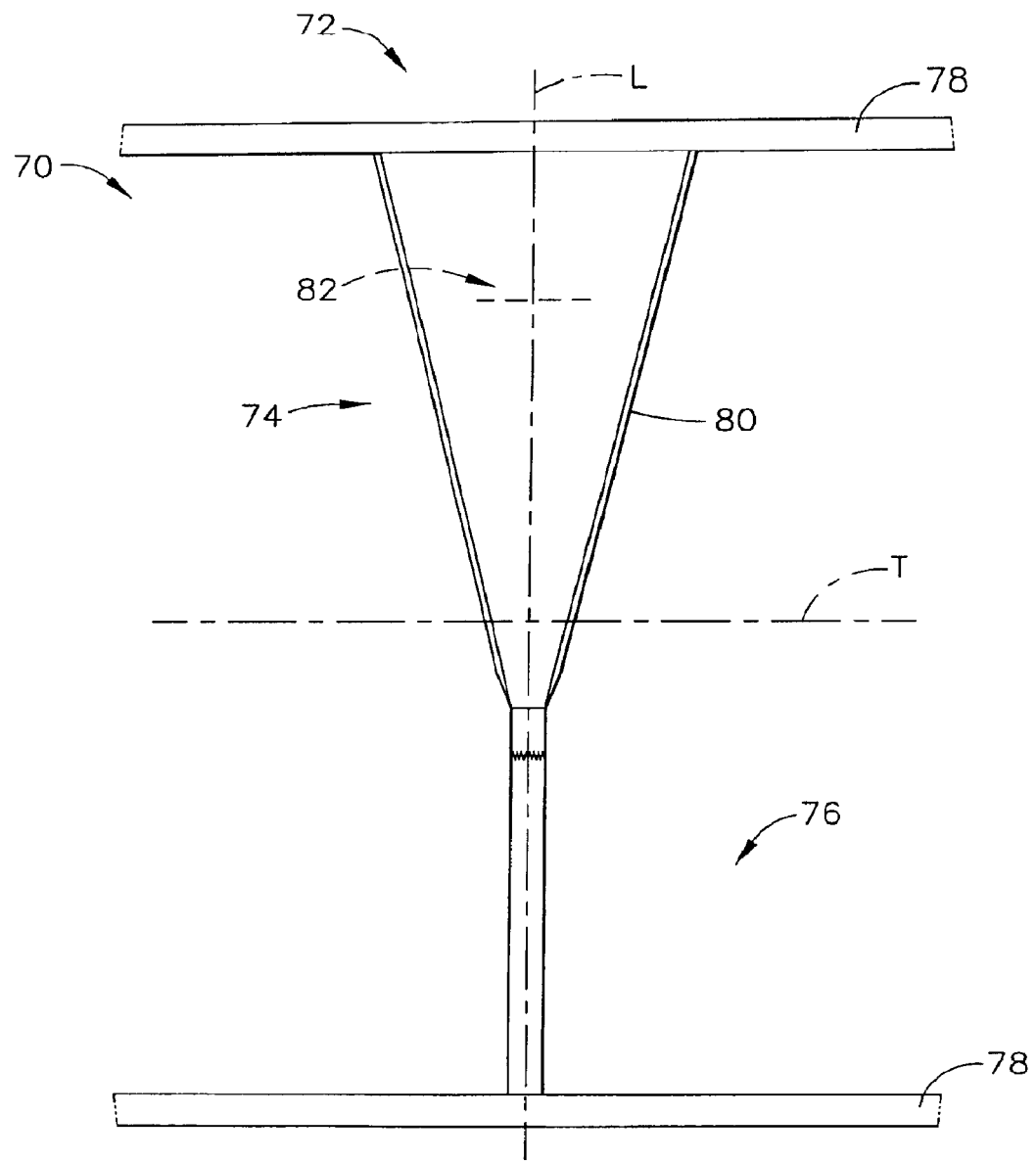
FIG. 4 is a plan view of another holder of the invention that has been opened at the sides, with the elastic components pulled flat.

In one embodiment, the side elastics are substantially straight (e.g., having a low degree of curvature) in the crotch region of the holder, such as shown in FIGS. 3 and 4. These substantially straight side elastics facilitate the use of long wings to better hold the article, such as a sanitary pad, in place and cover more of the side elastics. As known in the art, long wings enhance the soiling prevention performance provided by a sanitary pad. With non-thong shaped undergarments (e.g., briefs, bikinis, etc.), the relatively high curvature of the side elastic limits the practical length of the wings and therefore reduces the soiling prevention performance of the pad.

The side elastics 62 may be joined to the front region 30, the rear region 40, and the crotch region 50 about the periphery of the leg opening 60 using methods known in the art, e.g., using adhesive means or by mechanical means, such as stitching. The side elastics may be joined to portions of the side edges 25, 26, 27 and 28 surrounding the leg openings (i.e., that form the periphery thereof). Alternately, the side elastics may be integrally formed, for example, formed during the knitting process, using methods known in the art. For a knit holder, the side elastics are typically joined to the front region, the rear region and the crotch region by stitching.

The crotch region 50 of the holder 20 can also be provided with indicia, e.g., "placement guides" or "position guides", to help a wearer optimally position a compatible or coordinated article therein. Such indicia can comprise markings along the longitudinal centerline L of the holder to help a wearer reliably position the article on the inner surface of the crotch region. Placement guides 64 shown in FIGS. 1, 3 and 8 and placement guides 82 shown in FIG. 4 are examples of such indicia. Alternatively, the indicia can comprise markings on the side elastics 62 and 80 in the crotch region of the holder to help a wearer properly position wings on the article.

FIG. 4 is a plan view of an alternative holder 70 of the invention shown in a full flat out position with each of the sides opened and elastic components pulled flat. The holder has a longitudinal centerline L and a lateral centerline T. The holder comprises a front region 72, a crotch region 74 attached to the front region, and a rear region 76 attached to the front region and the crotch region. The rear region extends up the gluteal grove of the wearer, and cooperates with the front region to provide an adjustable waistband, such as elasticized waistband 78. The holder is also provided with side elastics 80 along the periphery of the crotch region to improve its fit. The holder further comprises placement guides 82 along its longitudinal centerline L to help the wearer position an article such as a sanitary pad on the inner surface of the crotch region of the holder. In one embodiment, the front, crotch and rear regions of the holder are comprised of the same material, such as the knit spandex material described above. The waistband may comprise the same or different material.

It will be appreciated that the holder herein may have other configurations besides those shown and described. For example, the front region may comprise one or more additional straps, strings, panels, or cut-out areas between the crotch region and the adjustable waistband. Other holder styles, designs, and configurations, such as "bikini", "briefs", etc., that comprise the front, crotch, and rear regions herein are within the scope of the present invention. As described above, the holder may comprise at least one extension or panel extending beyond the front, crotch, and/or rear regions so long as it does not significantly interfere with the function of the holder.

The holder of the invention can be made by various methods known in the art. Typically, a blank for the holder is first knit in a tubular form using means known to the art. For example, the front region 30, the rear region 40, and the crotch region 50 of holder 20 can be integrally knit. Appropriate knit patterns as described above can be used. In one embodiment, portions of the tubular knit blank are cut out to provide the leg openings 60 of holder 20. For example, a tubular blank can be flattened such that the interior faces thereof contact each other and a pair of longitudinally oriented side edges are formed. Leg opening precursors can then be formed by cutting matching portions having a semi-circular, semi-elliptical, or other desired shape from transversely opposite side edges at regular intervals along the flattened blank. Holder blanks are then formed by transversely cutting the flattened tubular blank in a predetermined repeat pattern wherein a first transverse cut is made across the material not removed when the leg opening precursors are formed to create a crotch portion precursor, and a second transverse cut is made across the full width of the flattened tubular blank forming the waist opening 21. The leg elastics 62 are disposed about the periphery of each leg opening and joined thereto. The two ends formed by the first transverse cut are joined by a single transverse seam to complete the crotch region 50. The holder 20 is then finished by forming a turned welt elasticized waistband about the periphery of the waist opening.

Alternatively, a tubular blank for the holder 20 can be slit walewise and opened. Excess material that would otherwise fill the leg openings 60 is removed to form a flat blank for the holder having a front end edge 23, a rear end edge 24, front side edges 25 and 26, and rear side edges 27 and 28. The side elastics 62 are joined to the holder about the periphery of the leg openings as discussed above. The blank for the holder is then folded about the lateral centerline T, and opposing portions of the side edges that lie between the leg opening and the end edges 23 and 24 are joined (e.g., by sewing the edges) to form seams at sides 32 and 34 completing the assembly of the holder. In one embodiment, the portion of side edge 25 that lies between the end of the side elastic 62 in the front region and the end edge 23 is joined to the portion of side edge 27 that lies between the end of the side elastic in the rear region and the end edge 24 to form a seam at side 32. Side edge 26 is joined to side edge 28 in a similar manner to form a seam at side 34.

The holder of the present invention can be used with a wide variety of compatible articles, particularly absorbent articles, including sanitary pads, pantiliners, interlabial inserts, urinary incontinence pads, diaper inserts, fluid collection bags and other devices, and the like, capable of being held in close bodily contact in the pudendal region of the wearer. Such an article has a compatible shape and size, and typically fits within the low-motion zone of the wearer and avoids significant leg movement interactions that can interfere with close bodily contact in the pudendal region. The invention thus provides a system comprising the thong-shaped holder herein and a compatible article for use therewith. While not intending to be limited by theory, it is believed that the article/holder system provides improved performance because the holder maintains the article (e.g., a pad) in close bodily contact in the pudendal region of the wearer, both the article and the holder fit within the low-motion zone of the body, and/or the article and holder are designed to work together in a coordinated manner.

Figure 5:
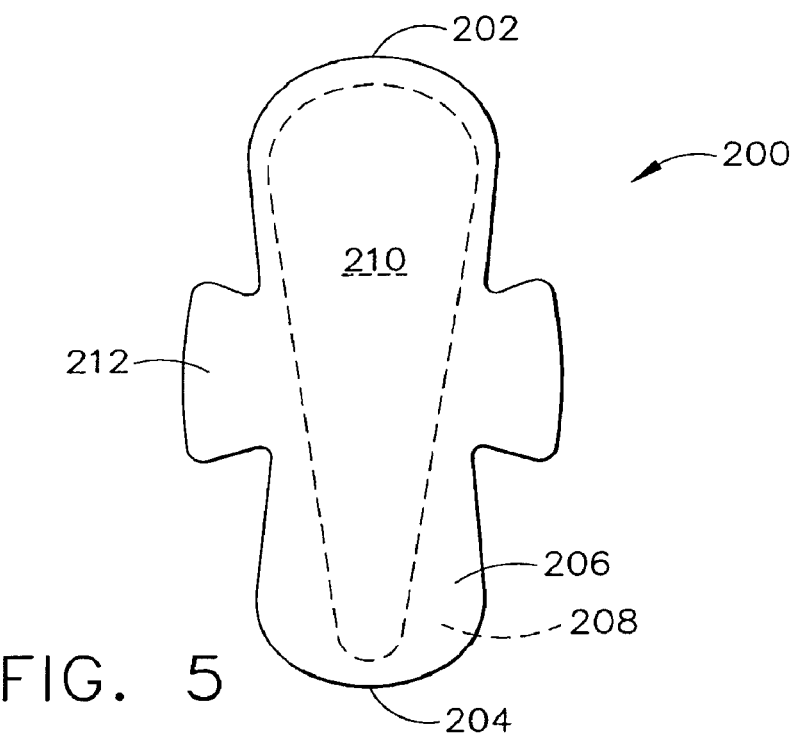
FIG. 5 is a plan view of a sanitary pad suitable for use with a holder of the invention.
Figure 6:
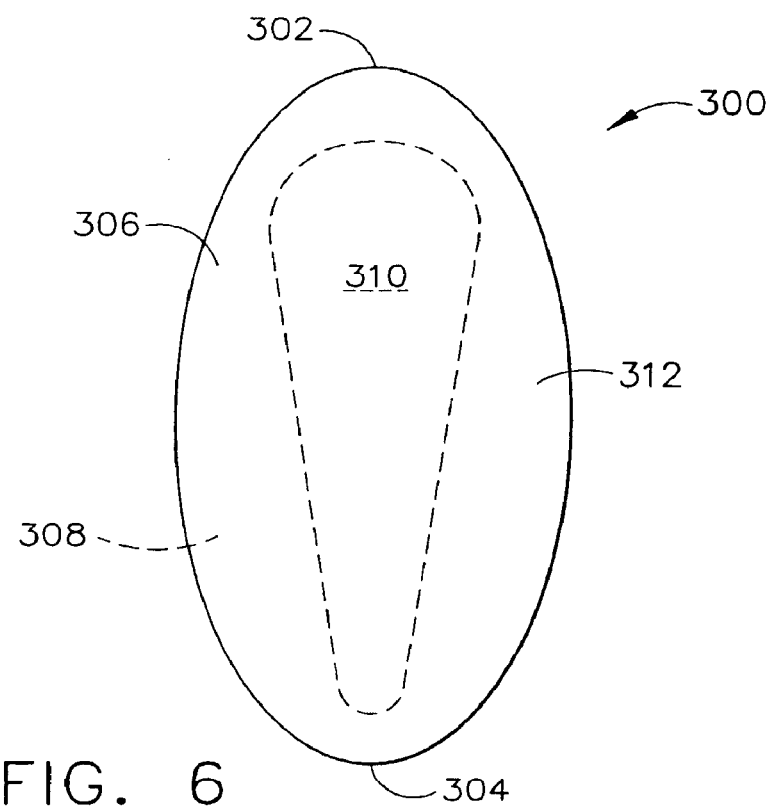
FIG. 6 is a plan view of another sanitary pad suitable for use with a holder herein.

FIG. 5 is a plan view of one such compatible absorbent article suitable for use in the system of the present invention. In this embodiment, the absorbent article is a thong-shaped sanitary pad designated 200. In one embodiment, the absorbent article has an absorbent capacity of at least about 8 grams of fluid, typically at least about 20.0 grams of fluid, and more typically at least about 40.0 grams of fluid. In another embodiment, the article has a caliper of greater than about 5.0 mm, typically greater than about 7.0 mm, and more typically greater than about 10.0 mm. FIG. 6 is a plan view of another compatible absorbent article for use in the present system. In this embodiment, the absorbent article is an oval shaped sanitary pad designated 300. Other compatible absorbent articles for use herein are shown in FIGS. 7-24. Other compatible articles are also described in U.S. Pat. No. 6,393,621, Redwine et al.; U.S. Pat. No. 6,582,411, Carstens, et al.; PCT Application WO 99/25289; U.S. Pat. No. 5,354,400, Lavash, et al.; and U.S. Pat. Nos. 4,687,478 and 5,267,992, Van Tilburg; all incorporated herein by reference.

An article herein has at least two surfaces, a liquid pervious side, i.e., a body-contacting surface or "body surface", and a liquid impervious side, i.e., a holder-contacting surface, opposite the liquid pervious side. The body surface is worn adjacent to the wearer's body. The holder surface is placed adjacent to the supporting holder when the article is worn. An absorbent article typically also comprises an absorbent component, such as an absorbent core, between the liquid pervious side and the liquid impervious side. The liquid pervious and impervious sides are arranged to form a unitary structure, with the absorbent component therebetween. An absorbent article herein will be described in detail with reference to the sanitary pad 200 shown in FIG. 5.

The sanitary pad 200 has two centerlines, a longitudinal centerline and a lateral centerline. The term "longitudinal" refers to a line, axis or direction in the plane of the pad that is generally aligned with (e. g., approximately parallel to) a vertical plane that bisects a standing wearer into left and right body halves when the pad is worn. The term "lateral" refers to a line, axis or direction that lies within the plane of the pad that is generally perpendicular to the longitudinal direction.

Figure 7:
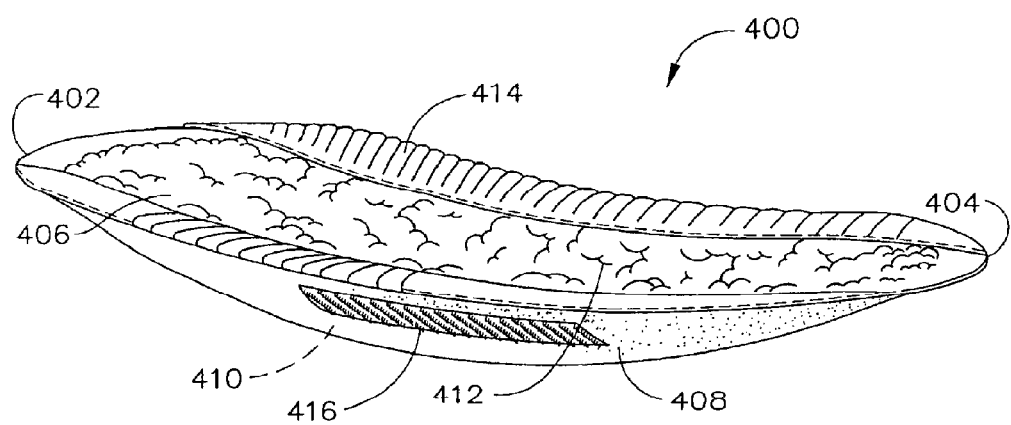
FIG. 7 is a perspective view of another sanitary pad suitable for use with a holder herein.

The sanitary pad 200 has two spaced apart side edges, and two spaced apart end edges (or "ends"), which together form the periphery of the absorbent article. When worn, the front edge 202 of the pad lies in a position anterior to the introitus and the rear edge 204 lies posterior to the perineum. In the embodiment shown in FIG. 5, the pad has a generally flat configuration. However, other suitable configurations, including cup-shaped configurations such as shown in FIG. 7 and disclosed in U.S. Pat. No. 6,582,411, may be used.

The article and any absorbent core may have any suitable plan view configuration, including, but are not limited to: thong-shaped; oval; race-track shaped; and shapes that have convexly-inward longitudinal side edges (e.g., hourglass shapes). In the embodiment shown in FIG. 5, the sanitary pad and its primary absorbent core have a thong-shaped configuration with straight side edges and convexly curved end edges.

An absorbent article typically has an absorbent capacity of at least about 20 grams of fluid. Other absorbent articles for use herein may have more or less absorbent capacity. Such articles can be designed to meet different absorbency needs ranging from a pantiliner having an absorbent capacity of less than about 5 grams of fluid to an incontinence pad having a capacity of more than about 60 grams of fluid.

The absorbent article typically comprises at least three primary components: a liquid pervious topsheet, a liquid impervious backsheet, and an absorbent component such as an absorbent core positioned between the topsheet and the backsheet. The liquid pervious topsheet, the liquid impervious backsheet, and the absorbent component can comprise a number of suitable materials provided that the absorbent article has the overall characteristics described herein.

It should be understood that articles herein are not limited to structures that have these three primary components. Articles can be provided that only have one or two of these components, or have additional components. For example, an absorbent article need not have a topsheet if the body-contacting surface of the absorbent core is suitable for use as a topsheet. A liquid impervious component, such as a liquid impervious backsheet, could be joined to the other side of the absorbent component. Alternatively, an absorbent article can comprise an absorbent component that has a liquid pervious side and a liquid impervious side. The liquid impervious side can be provided by treating the holder-contacting surface of the absorbent component to render it liquid impervious.

While the articles described herein and any component topsheet, absorbent core and backsheet materials are typically disposable, they may be designed to be cleaned, laundered, restored, and/or reused after use. The article may thus comprise washable, reusable material.

Absorbent articles such as sanitary pads are often worn in a loose-fitting undergarment. Such pads are typically designed to be large enough so that in the event of any shifting of the pad from its position under the vaginal introitus, it will still be able to intercept the wearer's bodily discharges. If an absorbent article with sufficient absorbent capacity is held closely against the wearer's pudendal region, and in particular covers the vaginal introitus, the surfaces of the labia majora, and the perineum, the article can be of a reduced size. Such an absorbent article need only be large enough to cover these regions of the wearer's body, rather than being sized to accommodate shifting of the article with respect to the introitus. The article and holder herein typically function by capturing body fluids at or near their source, using comfortable forces to hold the article in place at the source of the body fluids.

The sanitary pad 200 typically is capable of maintaining contact with at least a portion of the exterior surfaces of the wearer's labia, and at least a portion of the crotch region of the holder 20. The pad typically covers an area of the wearer's body that is centered about the wearer's labia and has a projected width of at least about 2.54 cm. The pad may cover substantially all of the exterior surfaces of the wearer's labia. The pad typically does not cover areas of the wearer's body that undergo substantial degrees of movement (i.e., the pad is placed adjacent to the low-motion zone of the wearer's body). In particular, the side edges of the pad typically do not have substantial contact with the inside surfaces of the wearer's thighs when the wearer walks or otherwise moves about. This overcomes a drawback of larger-sized sanitary pads that typically transfer forces applied to their edges to other portions of the pad, causing it to bend, crumple, and/or shift from the desired position under the wearer's vaginal introitus.

The sanitary pad 200 can be made somewhat larger if the edge portions thereof that may contact the inside surfaces of the wearer's thighs do not substantially transfer forces acting thereon to the remainder of the pad so as to cause it to bend, crumple, and/or shift from the desired position under the wearer's vaginal introitus. For example, an absorbent article can be constructed to have the desired target absorbent region described herein (e.g., covering the pudendal region and the perineum), with one or more additional regions located outboard of the target absorbent region that are suitably flexible and merely serve a "drop cloth" function with minimal or no absorbency. Such additional regions can be comprised of topsheet and backsheet materials, and possibly a thin layer of absorbent material therebetween. Such regions can serve as "wings" when they extend laterally from the central absorbent component and are folded around the side edges of the holder.

The liquid pervious side of the article herein is the body-contacting surface of the article. The liquid pervious side typically comprises a standard nonwoven web. Suitable fibers useful for making such a nonwoven web include polyolefin and polyester fibers. The nonwoven web typically has a basis weight from about 20 to about 200 grams per square meter, e.g., from about 30 to about 100 grams per square meter.

In some embodiments, the liquid pervious side comprises a plurality of elements extending outward from the body-contacting surface of the absorbent article. If the body-contacting surface is considered to lie within the X-Y plane, these elements will extend outward from this plane in the Z-direction. These elements can form any suitable angle with the body-contacting surface of the article. The elements can comprise any suitable type of components, including, but not limited to, fibers.

In one embodiment, the liquid pervious topsheet comprises a high loft fibrous material. The term "high loft fibrous material" refers to a low density, but relatively high caliper, fibrous material. The high loft fibrous material typically has a density of less than or equal to about 0.01 g/cm$^3$, and a caliper of greater than or equal to about 3.2 mm, typically between about 6.4 mm and about 13 mm. The high loft fibrous material typically has a basis weight of less than or equal to about 142 grams/m$^2$. The calipers and densities for such material are measured under INDA standard test method IST 720.1-92, which specifies measuring caliper under a pressure of 350 Pa.

The high loft fibrous material often comprises of fine polymeric fibers, which typically have a denier per fiber of less than or equal to about 6. The high loft fibrous topsheet material serves several functions. It allows the article to achieve a "macro" fit that is capable of fitting virtually all women, and a "micro" fit that adjusts to the particular body contours (which may be in the form of rugosities) of individual women. Another advantage of the high loft topsheet is that it is very soft and "cushiony". The high loft topsheet also is advantageous because it has a low coefficient of friction against the wearer's body due to the discrete contact of the individual fibers with the wearer's body.

In some embodiments, the high loft topsheet comprises a thermally bonded polyester fibrous nonwoven material having a caliper of about 4 mm and a basis weight of about 50 grams/$m^2$. The fibers of this high loft topsheet material are typically in a random orientation. One particular material for the high loft topsheet has a caliper of 4.1 mm and a density of 0.0077 g/$cm^3$. Another high loft topsheet material has a caliper of 5.8 mm and a density of 0.0098 g/$cm^3$ (after rebulking). If the high loft topsheet material has one side that is relatively flat and one side that is "fluffy", the flat side is typically oriented toward the absorbent core of the article.

In other embodiments, the liquid pervious topsheet may comprise an apertured film, such as an apertured, formed film. Suitable formed films are described in U.S. Pat. No. 3,929,135, Thompson; U.S. Pat. No. 4,324,245, Mullane, et al.; U.S. Pat. No. 4,342,314, Radel, et al.; U.S. Pat. No. 4,463,045, Ahr, et al.; and U.S. Pat. No. 5,006,394, Baird; all incorporated herein by reference. One material for the topsheet comprises a formed film described in one or more of the above patents and marketed on sanitary pads by The Procter & Gamble Company as the "Dri-Weave". The topsheet typically has a hydrophilic surfactant incorporated therein during manufacture. One apertured film suitable for use as the topsheet is marketed on sanitary pads by The Procter & Gamble Company as "Cotton-Like Dri-Weave". Additional web materials suitable for use as the topsheet include apertured and non-apertured nonwoven materials, composite structures, and the like.

It is often assumed that leakage of menses from conventional sanitary pads occurs primarily as a result of the capacity of the absorbent article being exceeded. However, a substantial number of soiling accidents occur as a result of menstrual fluid that does not even enter the sanitary pad. Often these soiling accidents result from menses flowing adjacent to the wearer's body, and which may flow in or close to the wearer's pubic hair. By holding the surface of the sanitary pad in close bodily contact, the pad intercepts menses flowing along the wearer's body and allows such exudates to be acquired into the absorbent core. Topsheets may be designed to provide a capillary structure within each fiber as well as between fibers that enhances the capture of bodily fluids, such as menses, and directs such fluids into the sanitary pad.

The absorbent core may be manufactured in a wide variety of sizes and shapes (e. g., rectangular, thong-shaped, oval, hourglass, dog bone, asymmetric, etc.), and from a wide variety of absorbent materials commonly used in sanitary pads and other absorbent articles. The absorbent core, however, should typically be adapted so that it has the capacity specified herein. Examples of suitable absorbent materials include comminuted wood pulp, generally referred to as airfelt; creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; cotton cloth; or any similar material or combinations of materials, or mixtures thereof. The configuration and construction of the absorbent core may also be varied. For example, the absorbent core may have varying caliper zones, e.g., it may be profiled to be thicker in the center, or may comprise hydrophilic gradients, superabsorbent gradients, or lower density and lower average basis weight acquisition zones, or it may comprise one or more layers or structures.

The backsheet of the article herein can be any suitable flexible, liquid impervious material. Typically, the backsheet is a polyethylene film having a thickness of from about 0.013 mm to about 0.05 mm. Suitable polyethylene films are manufactured by Clopay Corporation under the designation P18-0401 and microflex 1401. The backsheet may he embossed and/or matte finished to provide a more cloth like appearance. Further, the backsheet may permit vapors to escape from the absorbent core (i.e., it may be breathable) while still preventing exudates from passing through the backsheet. A suitable breathable backsheet material comprises an adhesively attached laminate of an apertured film having tapered capillaries, such as that described in U.S. Pat. No. 3,929,135, Thompson, and a microporous film. A suitable microporous film is supplied by Exxon Chemical USA, and described in U.S. Pat. No. 4,777,073, Sheth. The breathable backsheet is typically arranged so that the smaller openings of the tapered capillaries face the absorbent core. The microporous film is joined to the side of the apertured film having the larger openings to form the holder-contacting surface of the absorbent article. In one embodiment, both the absorbent article and the crotch region of the holder are vapor permeable.

Sanitary pads and other absorbent articles herein often comprise wings or flaps that extend laterally from a central absorbent component and are folded around the edges of the holder in the crotch region. The wings typically are provided with an attachment means (e.g., adhesive) for affixing the wings to the outside of the holder in the crotch region. The wings cover the sides of the holder and minimize or prevent exudate soiling of the holder in these covered areas. Typically, longer wings provide better side soiling protection. Because of the substantially straight side elastics in the crotch region of certain holders herein, the wing length of a coordinated pad can be maximized. The wings may also help stabilize the absorbent article and prevent it from shifting out of place, especially when the wings are affixed to the outside of the holder. Therefore, longer wings are also desirable to improve the stability and "stay-in-place" performance of the absorbent article. The stability of longer wings, combined with increased side coverage, further improves the soiling protection provided by the system of this invention. In one embodiment, the absorbent article comprises wings having a length at least about 75%, typically at least about 80%, and more typically at least about 85% (e.g., at least about 90%) of the length of the absorbent article. Suitable wings are described in U.S. Pat. Nos. 4,687,478 and 5,267,992. Van Tilburg, and in U.S. Pat. No. 5,354,400, Lavash, et al., all incorporated herein by reference.

In another embodiment, the absorbent article comprises such long wings and a primary absorbent core having a width less than or equal to the width of the crotch region of the holder. As used herein, the width of the absorbent core relative to the width of the crotch region of the holder is measured when the article is placed in the holder as it is intended to be worn. In one embodiment, the primary absorbent core has a width at least about 5.0 mm less than the width of the crotch region of the holder along at least a portion of the absorbent article's length, typically along a majority of the absorbent article's length, and more typically along substantially all of the absorbent article's length. The primary absorbent core typically has a width at least about 10.0 mm less, and more typically at least about 15.0 mm less (e.g., at least about 20.0 mm less), than the width of the crotch region of the holder along at least a portion of the absorbent article's length, typically along a majority of the absorbent article's length, and more typically along substantially all of the absorbent article's length. The combination of long wings and such a wider crotch region than the primary absorbent core often provides a barrier leg cuff configuration that improves containment of body exudates by the side elastics in the crotch region of the holder. In embodiments having thicker absorbent cores, more narrow absorbent cores and/or wider holder crotch regions can be selected to improve containment by such barrier leg cuff configurations.

The topsheet, the backsheet, and the absorbent core may be assembled in a variety of configurations known in the art, including layered or "sandwich" configurations and wrapped or "tube" configurations. In one embodiment, the sanitary pad 200 is assembled in a sandwich construction in which the topsheet and the backsheet have length and width dimensions generally larger than those of the absorbent core. The topsheet and the backsheet extend beyond the edges of the absorbent core to form portions of the periphery.

The topsheet may be joined to the body-contacting side of the absorbent core. In other embodiments, the topsheet need not be joined to the absorbent core to enhance the flexibility of the sanitary pad. The term "joined" encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. The backsheet need not be, and typically is not, joined to the absorbent core to enhance the flexibility of the absorbent article. The portions of the topsheet and backsheet that extend beyond the edges of the absorbent core to form the periphery are typically joined to each other. If the topsheet is joined to the absorbent core, it can be joined to the core in any suitable manner known in the art. The topsheet may be joined to the core by a uniform continuous layer of adhesive, a patterned layer of adhesive, or an array of separate lines, spirals, or spots of adhesive.

At least the liquid pervious side and the liquid impervious side of the absorbent article are arranged to form a "unitary structure." The term "unitary structure" refers to a construction in which the components are joined together, or integrated together as a unit. The term includes constructions such as those described above where the topsheet, absorbent core, and backsheet comprise separate components that are joined together. It also covers constructions in which the liquid pervious side and liquid impervious side of the absorbent article do not comprise a separate topsheet and/or backsheet. For example, in the latter case, the liquid pervious side, the liquid impervious side, or both, may comprise a surface of the absorbent core that has the desired characteristics, rather than a separate component.

FIGS. 5-24 show various absorbent articles suitable for use with thong-shaped holders of the present invention. Sanitary pad 200 shown in FIG. 5 comprises front edge 202, rear edge 204, and adjoining side edges that together form the periphery of the pad. The pad also comprises a topsheet 206, a backsheet 208, and a primary absorbent core 210 that has a generally trapezoidal shape, with substantially straight side edges that taper to a narrowed width near the rear edge 204. The primary absorbent core comprises the significant absorbent material for fluid acquisition and storage, and typically is located directly beneath the vaginal introitus as worn. In one embodiment, the primary absorbent core 210 has a length of about 21.0 cm, a width near the front edge 202 of the pad of about 6.5 cm, and a width near the rear edge 204 of the pad of about 2.2 cm. The primary absorbent core also typically has a width that is less than the width of the crotch region of the holder that will be used to hold the article. The pad thus has a size and shape compatible with the holder so that it can be held in close bodily contact in the pudendal region.

The pad 200 also comprises two side wings 212 that extend laterally from the central portion of the pad. The wings can be folded around the edges of the holder in the crotch region to help stabilize the pad and prevent it from shifting out of place. The wings typically have a fastening system such as an adhesive or other attachment means to help secure them to the outer surface of the holder in the crotch region.

In the embodiment shown in FIG. 6, sanitary pad 300 comprises front edge 302, rear edge 304, and adjoining side edges that together form the periphery of the pad. The pad also comprises a topsheet 306, a backsheet 308, and a primary absorbent core 310 that has a generally trapezoidal shape, with substantially straight side edges that taper to a narrowed width near the rear edge 304. In pad 300, the primary absorbent core 310 has a length of about 21.0 cm, a width near the front edge 302 of the pad of about 6.5 cm, and a width near the rear edge 304 of the pad of about 2.2 cm. The primary absorbent core also typically has a width that is less than the width of the crotch region of the holder. The pad thus has a size and shape compatible with the holder so that it can be held in close bodily contact in the pudendal region.

The pad 300 also comprises two side wings 312 that extend laterally from the central portion of the pad. The wings can be folded around the edges of the holder in the crotch region to help stabilize the pad and prevent it from shifting out of place. The wings typically have a fastening system such as an adhesive or other attachment means to help secure them to the outer surface of the holder in the crotch region. Wings 312 are longer than wings 212 shown in FIG. 5, and give the pad 300 a generally oval shape. Such long wings improve the stability of the pad and, since they cover more of the holder, better protect it and outer garments from soiling.

Another absorbent article useful herein is described in U.S. Pat. No. 6,582,411, Carstens et al., incorporated herein by reference. In the embodiment shown in FIG. 7, the article is a sanitary pad 400 capable of cupping the wearer's labia from the front of the labia to the back of the labia, although other configurations, including flat configurations, are possible. Pad 400 comprises front edge 402, rear edge 404, and adjoining side edges that together form the periphery of the article. The pad also comprises a topsheet 406, a backsheet 408, and a primary absorbent core 410 positioned between the topsheet and the backsheet. The absorbent component, such as absorbent core 410, typically is of a size and configuration to cover the wearer's pudendal region and perineum, and does not extend forward beyond the wearer's mons pubis or rearward to the wearer's anus. The pad is of a size to substantially cover all of the exterior surfaces of the wearer's labia. The pad typically has a flexure resistance of less than or equal to 100 grams and is capable of substantially maintaining sustained contact with and covering at least a portion of the inside surfaces of the wearer's labia, at least a portion of the exterior surfaces of the wearer's labia, and at least a portion of the holder. The pad 400 typically has a length of less than or equal to about 18 cm, and a surface area of less than or equal to about 130 $cm^2$. The primary absorbent core also typically has a width that is less than the width of the crotch region of the holder used to hold the pad.

Figure 8:
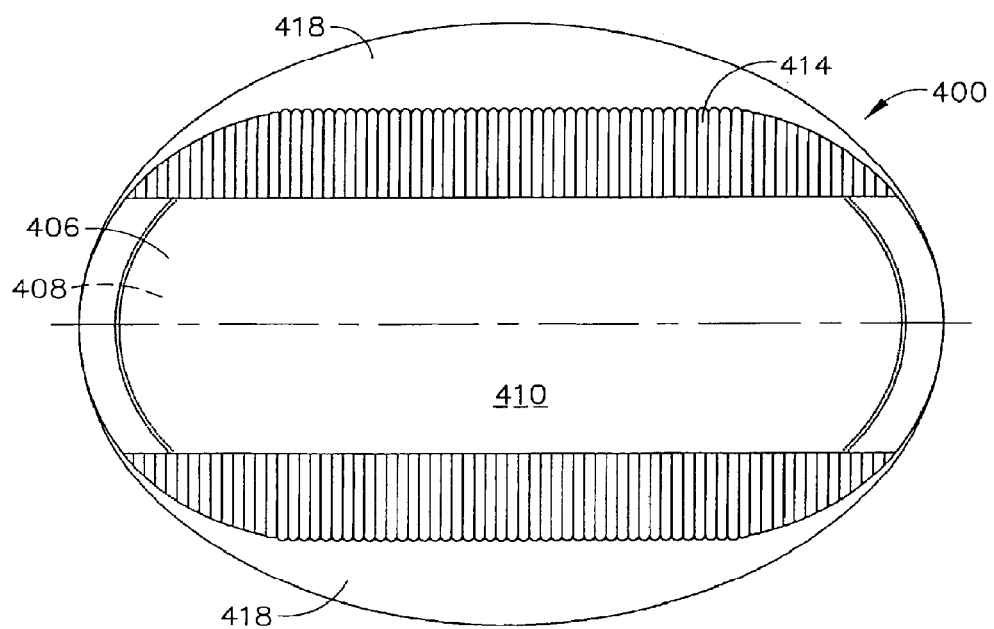
FIG. 8 is a top plan view of the pad of FIG. 7, further comprising wings.

In one embodiment, the pad 400 has an absorbent capacity of greater than or equal to about 10 grams of fluid in an area measuring 5 cm by 13 cm that will be centered under the vaginal orifice when the absorbent article is worn. In another embodiment, the pad has a capacity in said area of greater than or equal to about 20 grams of fluid. The ratio of absorbent capacity to surface area is often greater than or equal to about 0.3 g/cm$^2$. The liquid pervious topsheet side 406 of pad 400 may comprise a high loft fibrous material, and typically comprises a plurality of fiber elements extending outward from the body-contacting surface of the topsheet, such as fibers 412 shown in FIG. 7. The pad may further comprise a fastening system, such as mechanical fastening material 416, on the holder-contacting surface of the pad for engaging at least a portion of the holder. The pad may also comprise elastic members 414 wrapped around the side edges of the pad to form the desired cup-shaped configuration and provide soft side edges that contact the wearer during use. The soiling-prevention performance of such a pad may be enhanced with the addition of wings, particularly long wings (e.g., wings having a length of at least about 75% of the length of the pad). FIG. 8 is a top plan view of the pad of FIG. 7 with the addition of long wings 438.

Figure 9:
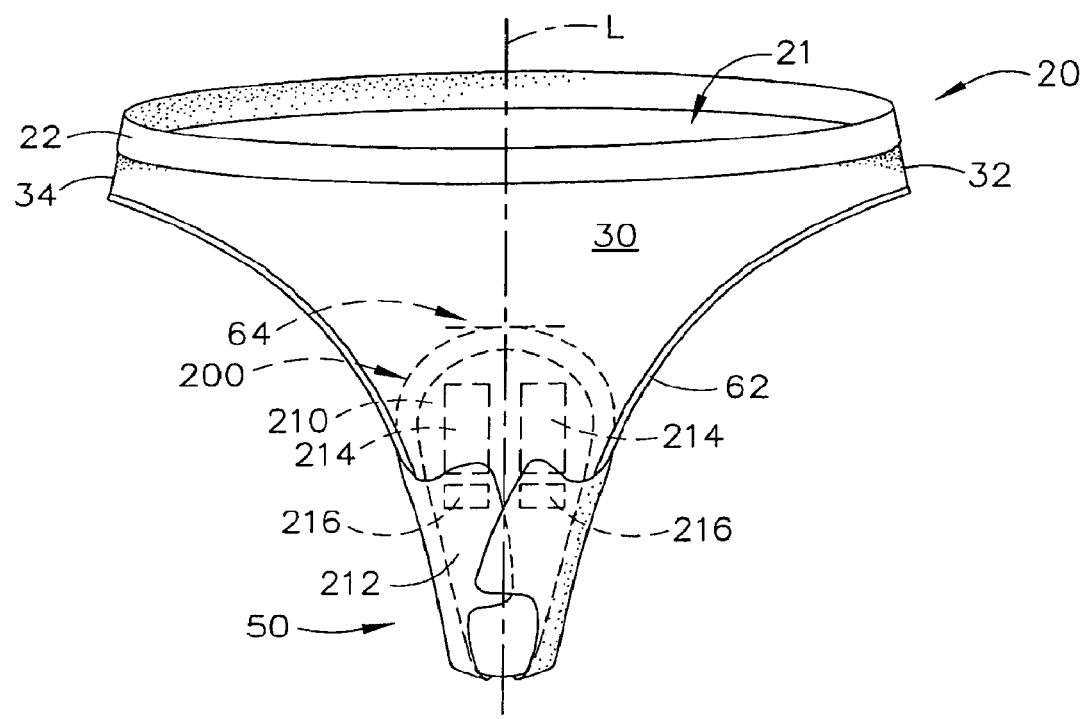
FIG. 9 is a front view of the pad of FIG. 5 further comprising fastening systems and worn with the thong-shaped holder of FIG. 1.

FIG. 9 is front view of the sanitary pad 200 of FIG. 5 further comprising fastening systems 214 and 216, and worn with the holder 20 of FIG. 1. FIG. 9 thus illustrates a system of the present invention. Other systems herein are obtaining by combining the articles of FIGS. 5-24 and other articles described herein with the various holders described herein. In the embodiment of FIG. 9, fastening system 214 is added to at least a portion of the liquid impervious side of the pad 200 to engage at least a portion of the body-contacting side of the crotch region of holder 20. Fastening system 214 may comprise any suitable fastening material, including an adhesive material, a cohesive-adhesive material, a material having a high coefficient of friction, or a mechanical fastening material. The wings 212 of pad 200 are shown folded around the edges of the holder in the crotch region and secured to the outer, garment-contacting side of the holder. In FIG. 9, the wings also have a fastening system 216 added to at least a portion of their liquid impervious side to engage at least a portion of the crotch region of holder 20. Fastening system 216 may also comprise any suitable fastening material, including an adhesive material, a cohesive-adhesive material, a material having a high coefficient of friction, or a mechanical fastening material. Although pad 200 in FIG. 9 comprises both fastening systems 214 and 216, these are optional and one or both may be omitted. As can be seen, the pad has a size and shape compatible with the holder so that it can be held in close bodily contact in the pudendal region of the wearer. The primary absorbent core of the article typically is of a size and configuration to cover the wearer's pudendal region and perineum, and is capable of being held in close bodily contact by the holder.

Currently, a woman typically selects an undergarment of particular style, size, and design for everyday use. Those undergarments are often used with conventional sanitary pads for feminine hygiene. Consequently, manufactures of conventional sanitary pads must design their pads for use in thousands of different combinations of undergarment characteristics, dimensions, and material properties (i.e., crotch width, material, curvature, size, etc.). Additionally, the crotch regions of conventional undergarments are typically not designed to maintain pad-to-body contact. As a result, conventional undergarment/pad systems commonly used do not perform well for hygiene purposes. Because of the wide variation of undergarment products, many new absorbent articles with technical merit do not perform well with conventional undergarments and thus have not been utilized. The holders and systems of the present invention overcome many of these problems, and often enhance the performance of such absorbent articles.

The absorbent article and holder can be designed to work together in a coordinated and superior manner. For example, several absorbent fiber and structure inventions for absorbent articles require close pad-to-body contact for efficacy. These inventions have not been meaningfully beneficial when incorporated in sanitary pads because conventional undergarments do not reliably maintain the pad in close bodily contact. The absorbent article/holder system of this invention can be designed to utilize such improved absorbent articles and components because the holder reliably maintains the article in close bodily contact.

The absorbent article/holder system herein may also provide benefits in the area of absorbent article fastening. Conventional undergarment/absorbent pad systems typically expose the pad to high motion areas of the crotch region (i.e., leg interaction). When leg movement pushes the pad, it tends to move relative to the undergarment's crotch. To minimize this movement, pressure sensitive adhesives are utilized on the garment side of the pad to secure the pad to the crotch. The adhesive and covering "release paper" add cost to the pad and inconvenience to the user. There have been several fastening system inventions that replace pressure sensitive adhesive and release paper with non-adhesive fastening systems. However, these have not been meaningfully beneficial when incorporated in conventional undergarment/pad systems because the pads are exposed to high motion areas of the crotch region. The coordinated pad/holder system of the present invention can utilize these non-adhesive fastening systems since the pad and holder fit in the low motion zone of the body. The pad fastening surface and the holder crotch surface can also be coordinated and optimized to provide improved fastening.

The article/holder system of this invention can also reliably hold new forms of absorbent articles close to the body. Such articles perform better when held close to the fluid source and in close bodily contact. Several sanitary pads are said to provide close pad-to-body contact by attaching the pad directly to the skin and holding it in place by using pad-to-body interaction. Alternatively, the pad can be held in place with special body-adhesives. These pads perform even better when the present holder assists in holding the pads in close bodily contact, with or without special body-adhesives.

Compatible absorbent articles useful with the present holder are described in U.S. Pat. Nos. 5,383,869, 5,575,786, 4,950,264, and 5,009,653, Osborn III., incorporated herein by reference. In one embodiment, the article is a sanitary pad that is thin, relatively highly flexible, and has a capacity great enough to handle medium to high menstrual flows. The pad typically comprises, from the body surface down, an apertured formed film or nonwoven topsheet, a wipe acquisition sheet, a wet-laid tissue, a superabsorbent core, and a barrier backsheet. The pad often has an absorbent capacity, as defined herein, of at least about 8.0 grams of fluid, typically at least about 20.0 grams of fluid, and more typically at least about 40.0 grams of fluid. The pad typically has a caliper of less than about 5.0 mm, more typically less than about 3.0 mm, for example, less than about 2.6 mm. The pad typically has a flexure resistance of less than about 400 grams, more typically less than about 300 grams, for example less than about 250 grams. The performance of such a thin pad is enhanced when it is held close to the fluid source and in close bodily contact by the holder of this invention.

Another compatible absorbent article useful herein is described in U.S. Pat. No. 6,440,111, Berba et al., incorporated herein by reference. In one embodiment, the absorbent article is designed for collecting and/or absorbing low volumes of menstrual and non-menstrual bodily fluids. The article is particularly useful for everyday use for managing daily perspiration, vaginal discharge, post intercourse drainage, and other bodily fluids due to various conditions, such as infection. The article may comprise an absorbent-free, liquid permeable structure having a first surface and a second surface opposite thereof, and a barrier layer covering at least a portion of the second surface. The article may be substantially free of absorbent material, and will collect fluid within the interstitial spaces (pores) to prevent fluid from transferring to unwanted surfaces. The article may also comprise a liquid permeable cover, a barrier layer, and an absorbent core intermediate the cover and the barrier layer. The article may have an absorbent capacity of about 1.2 grams or less and a caliper of about 3.0 mm or less. In one embodiment, the absorbent core may comprise about 0.7 grams or less of absorbent material. The absorbent material typically is substantially free of superabsorbent polymers and absorbent gelling materials. The performance of such an article is enhanced when held close to the fluid source and in close bodily contact by the holder herein.

In one embodiment, the absorbent article has an absorbent capacity of less than about 10.0 grams of fluid, typically less than about 5.0 grams of fluid, and more typically less than about 3.0 grams of fluid, e.g., less than about 1.2 grams of fluid. The article may have a caliper of less than about 5.0 mm, typically less than about 3.0 mm, and more typically less than about 2.6 mm. The article may have a flexure resistance of less than about 250.0 grams, and typically less than about 120.0 grams.

Another compatible absorbent article for use with the holder of this invention is described in U.S. Pat. No. 5,382, 245, Thompson et al., incorporated herein by reference. In one embodiment, the article comprises a special fluid transport layer having external capillary channels that direct body fluids to a storage layer. The article has an absorbent core that is positioned between the topsheet and the backsheet. The core has an uppermost surface facing the topsheet and a lowermost surface facing the backsheet. A transport layer having a lower portion and an upper portion is positioned where the lower portion of the transport layer is below the uppermost surface of the core and is oriented substantially in the longitudinal direction. The upper portion of the transport layer extends at least to the uppermost surface of the absorbent core toward the topsheet and contains elements oriented substantially in the z-direction. The transport layer extends above the uppermost surface of the absorbent core. The performance of an absorbent article with such a fluid transport layer having external capillary channels is enhanced when the article is held close to the fluid source and in close bodily contact by the holder.

Another compatible absorbent article for use herein is described in U.S. Pat. No. 6,287,288, Osborn III et al., incorporated herein by reference. In one embodiment, the extensible absorbent article is capable of extending in length (i.e., in the longitudinal direction) and/or width (i.e., in the transverse direction), and/or in other directions. The absorbent article is typically capable of extending up to about 150% of its length or width under a force of 500 grams. The absorbent article may also be capable of extending beyond 150% of its original dimension. The performance of such an extensible article is enhanced when it is held close to the fluid source and in close bodily contact by the holder of this invention.

In one embodiment, a sanitary pad comprises an extensible liquid pervious topsheet, an extensible liquid impervious backsheet, and an extensible absorbent core positioned between the topsheet and the backsheet. The topsheet and backsheet are joined together around the periphery of the pad. The pad also comprises a fastener for attaching the pad to the crotch region of the holder. The fastener is capable of permitting at least portions of the pad to extend in the longitudinal direction. In some embodiments, the pad is comprised of extensible components and inextensible components. For instance, the pad may have an extensible topsheet and backsheet and an inextensible absorbent core that is slung between the extensible topsheet and backsheet. In one variation, the pad may have an inextensible topsheet as well. The pad may have stretch attachment means for fastening to the holder. In one embodiment, the pad has a center region that deflects upward when the pad is stretched. In another embodiment, the pad has a "pop-up" center. Other embodiments have regions of differential stretch that allow the pad to assume particular configurations during use.

As described above, the holder-contacting surface of the absorbent article typically comprises a fastening system for attaching the article to the holder. The fastening system may comprise an adhesive material, including any of the pressure sensitive adhesives typically used to secure conventional sanitary pads to the crotch region of undergarments. Alternatively, the absorbent article/holder system may comprise mechanical fastening material located on a portion of the liquid impervious side of the article that will engage with at least a portion of the crotch region of the holder. The mechanical fastening material can be located on any suitable portion of the holder-contacting surface of the article. The mechanical fastening material can be distributed in a pattern that matches the pattern of one or more pre-selected portions of the holder. The alignment of the mechanical fastening material with portions of the holder can be used as a placement guide to ensure that the article is positioned properly in the holder. The pattern of mechanical fastening material can also be used to assist in fitting the article closely against the wearer's body. If the article comprises wings, at least a portion of the wings may comprise mechanical fastening material for engaging at least a portion of the crotch region of the holder. For example, pad 200 shown in FIG. 9 comprises fastening systems 216 located on the liquid impervious side of wings 212. Fastening systems 216 may comprise mechanical fastening material for engaging at least a portion of the crotch region of holder 20.

The sanitary pad 200 is typically utilized by placing it in the crotch region of the holder 20, with one end extending toward the front region of the holder and the other end towards the back region of the holder. The backsheet of the pad is placed in contact with the inner surface of the center of the crotch region of the holder. Fastening systems 214, shown in FIG. 9 on the holder-contacting side of the sanitary pad, may comprise projections of mechanical fastening material for engaging with the knit material from which the crotch region of the holder is typically made. The wearer then pulls on the holder, which stretches and fits the wearer.

In one embodiment, the holder-contacting surface of the absorbent article comprises a skin-friendly mechanical fastening material having a substrate or surface with an array of prongs in the form of a plurality of small hair-like projections disposed thereon, such as described in U.S. Pat. No. 6,582, 411, Carstens, et al., incorporated herein by reference. For example, sanitary pad 400 shown in FIG. 7 comprises mechanical fastening material 416 on its holder-contacting surface. Such projections are capable of easily adhering to knit material (e.g., the crotch region of the holder), and have sufficient holding force even when the holder stretches and contracts.

Cohesive-adhesive fastening systems, such as described in U.S. Pat. No. 5,415,650, Sigl, et al., incorporated herein by reference, are also suitable for use herein. The absorbent article is positioned on and held secure to the crotch region of the holder by cohering a first cohesive-adhesive with the second cohesive-adhesive. For example, in FIG. 9, each of fastening systems 214 may comprise a) a first cohesive-adhesive at least partially impregnated or coated onto at least a portion of the liquid impervious side of the article, and b) a second cohesive-adhesive at least partially impregnated or coated on at least a portion of the crotch region of the holder. As used herein, a "cohesive-adhesive" material is one that preferentially adheres to itself and not to other materials. If the absorbent article comprises wings, the liquid impervious side of each wing and an exterior surface of the crotch region of the holder may be covered with a first and a second cohesive-adhesive, respectively, such that a first cohesive-adhesive present on the wings can cohere to a second cohesive-adhesive present on the exterior surface of the crotch region. For example, fastening systems 216 shown in FIG. 9 may comprise a first cohesive-adhesive on the liquid impervious side of the wings 212 for engaging a second cohesive-adhesive on the garment-contacting side of the crotch region of the holder. The holding force provided by the crotch region combined with the fit within the low motion zone enhances the absorbent article stay-in-place performance of cohesive-adhesive fastening systems relative to that of conventional pad/pant systems.

The absorbent article/holder system of this invention need not comprise any fastening adhesive or fastening material in order to hold the article in place. In one embodiment, the holding force provided by the crotch region of the holder combined with the frictional forces between the article and the holder are sufficient to hold the article in place, especially given the lack of relative motion in the low-motion fit zone of the body. Similarly, an absorbent article with wings need not comprise an adhesive or other fastening material on the wings to help keep them in place.

Another fastening system for use herein is described in U.S. Pat. No. 6,613,175, Moscherosch et al., incorporated herein by reference. In one embodiment, the absorbent article has a low auto-adhesion attachment means for maintaining the article's position in use. The article is capable of being folded upon itself prior to use, and then unfolded without destroying any aspect thereof. This eliminates the need for a separate release sheet to protect any positioning adhesive prior to use. This embodiment may reduce non-value-added costs, enhance consumer convenience by reducing the number of steps of use, enhance consumer discretion by eliminating release sheet handling issues such as noise and disposal, and reduce environmental concerns by eliminating a portion of the product from the solid waste stream. The holding force provided by the crotch region of the holder combined with the improved fit within the low motion zone enhances the stay-in-place performance of such low auto-adhesive fastening systems.

Another fastening system for use herein is described in U.S. Pat. No. 6,595,977, Luizzi, et al., incorporated herein by reference. The absorbent article comprises a high coefficient of friction (COF) surface on the liquid impervious side (e.g., backsheet) of the article to help maintain its in-use position. The holding force provided by the crotch region of the holder combined with frictional forces between such a high COF backsheet surface and the holder are sufficient to hold the article in place, especially given the lack of relative motion within the low-motion zone of the body. For example, in FIG. 9, each of fastening systems 214 may comprise a high COF surface on the backsheet 208 of the pad.

Another fastening system for use herein is described in U.S. Pat. No. 5,676,652, Hunter, et al., incorporated herein by reference. In one embodiment, the article has a pair of wings that are provided with mechanical fasteners. The wings extend laterally from a central absorbent component and are folded around the edges of the holder to provide coverage and reduce side soiling. The wings typically stay in place well enough to cover the side edges of the holder without affixing them underneath the holder. However, the wings may be provided with a skin-friendly mechanical fastening material for additional security.

The performance of such wings with mechanical fasteners may be enhanced by the absorbent article/holder system of this invention relative to conventional pad/panty systems because of one or more of the following reasons. First, the holding force provided by the crotch region of the holder combined with frictional forces between the article and the holder provides superior stay-in-place performance, especially given the lack of relative motion within the low-motion zone fit herein. Second, side elastics on the holder typically are substantially straight in the crotch region compared to the majority of conventional panties that have a high degree of curvature, which reduces the wings' propensity to stay wrapped. Such straight side elastics improve the wings' propensity to stay wrapped, thereby reducing the need for wing fastening strength. And third, since the article and holder are coordinated, the material in the crotch region on the garment-contacting side of the holder can be optimized to work effectively with the wings' mechanical fastener.

The absorbent article/holder system of this invention also can be used with forms of wings that automatically cover the edges of the holder (i.e., "auto-wrap" wings) without requiring action by the wearer to fold the wings, as required with conventional wings. Such "auto-wrap" wings are described in U.S. Pat. Nos. 5,584,829 and 5,354,400, Lavash, et al., incorporated herein by reference. The performance of such wings may be enhanced by the present holder and system because of one or more of the following reasons. First, the low motion zone fit provided helps maintain pad and wing "stay-in-place" performance, even with a high degree of body motion. Second, substantially straight side elastics herein help maintain "stay-in-place" performance of the wings, even without wing fastening means. Third, the coordinated nature of this system allows the wings to be designed in concert with the holder to maintain optimal performance.

In one embodiment, a sanitary pad has a wing that provides coverage to reduce side soiling without the use of conventional wings. The wing is joined to the main body portion of the pad and is wider than the crotch region of the holder. The wing has a pair of short, flexible (and in some embodiments, drapable) longitudinal side portions that extend beyond the crotch edge portions of the holder. The side wrapping elements have a high fold retention. The wing comprises at least some extensible portions that are provided with low or no return force (force that tends to cause the extensible portions to retract after they have been extended). The fact that the extensible portions are provided with low or no return force and the side wrapping elements have a high fold retention allows the side wrapping elements of the wing to automatically fold around the crotch edge portions of the holder toward the underside of the holder and to remain folded when the pad is placed in the holder and the holder is pulled up adjacent the wearer's body.

In another embodiment, an absorbent article such as a sanitary pad may have a region, typically centrally located, that is thicker and/or stiffer than portions that lie outboard of this center region. The pad may have a central low motion area that has a greater thickness and/or less flexibility than regions of the pad that may contact the insides of the wearer's thighs and experience more motion. The pad may have an additional raised portion on its body-contacting side. The raised portion is typically centered relative to the longitudinal centerline of the pad. The raised portion may extend any desired portion of the length of the pad, up to its full length. The raised portion can be formed by a variety of different types of structures. In some embodiments, the raised portion can comprise a tube of absorbent material that is joined to the liquid pervious side of the pad to form a compound absorbent article. In other embodiments, the raised portion can comprise a hump-forming element that may underlie the liquid pervious topsheet. Examples of absorbent articles having a raised portion on their body-contacting side are described in U.S. Pat. No. 6,582,411, Carstens et al., incorporated herein by reference.

Other absorbent articles having raised portions on their body-contacting side are described in U.S. Pat. No. 6,171,291, Osborn, III, et al.; U.S. Pat. No. 6,740,069, Drevik; and U.S. Pat. No. 6,316,688, Hammons, et al.; incorporated herein by reference. These articles maintain pad-to-body contact in conventional pad/panty systems by filling the gap between the body and pad surface with "humps" and "tubes" of absorbent material. When conventional sanitary pads are used with the wide variety of available conventional panties, the panty crotch frequently sags and the body-contacting pad surface separates from the body (i.e., pad-to-body contact is lost). When this gapping occurs, the pad does not absorb the body's exudates as effectively as when it maintains pad-to-body contact. Stuffing or filling these gaps with humps or tubes is one approach to maintain pad-to-body contact. However, such humps and tubes also frequently separate from the body, reducing their effectiveness.

The performance of absorbent articles comprising humps and/or tubes is enhanced by the article/holder system of this invention relative to conventional pad/panty systems because of one or more of the following reasons. First, the holding force provided by the crotch region of the holder effectively provides and maintains pad-to-body contact. Second, the low motion zone fit of this invention helps maintain pad-to-body contact, even with a high degree of body motion. Third, the coordinated nature of the system allows the absorbent hump or tube to be designed in concert with the holder to optimally position it against the body. This optimal positioning, combined with maintenance of pad-to-body contact, further improves absorbency performance versus conventional pad/panty systems.

In one embodiment, such as described in U.S. Pat. No. 6,171,291, Osborn III, et al., the absorbent article is provided with a longitudinal medial absorbent hump in the longitudinal central region on the body-contacting side of the article. The hump provides additional absorbent capacity and liquid acquisition capability in the target region of the article. The hump also typically maintains the article in close physical contact with the wearer's body. The article comprises a principal longitudinal centerline, a principal transverse centerline, a body surface, and a holder surface. A longitudinal central region is disposed along the length of at least a portion of the principal longitudinal centerline. The article has surrounding regions such as longitudinal side regions disposed at least laterally outboard of the longitudinal central region. The article comprises a liquid pervious topsheet, a liquid impervious backsheet joined to the topsheet, and an absorbent core positioned between the topsheet and backsheet. The longitudinal medial hump has a caliper measured at its point of maximum amplitude of greater than about 3.0 mm, typically between about 4.0 mm and about 15.0 mm. The hump typically has a base width of between about 0.5 cm and about 5.0 cm, and a length of between about 2.0 cm and about 12.0 cm.

Figure 10:
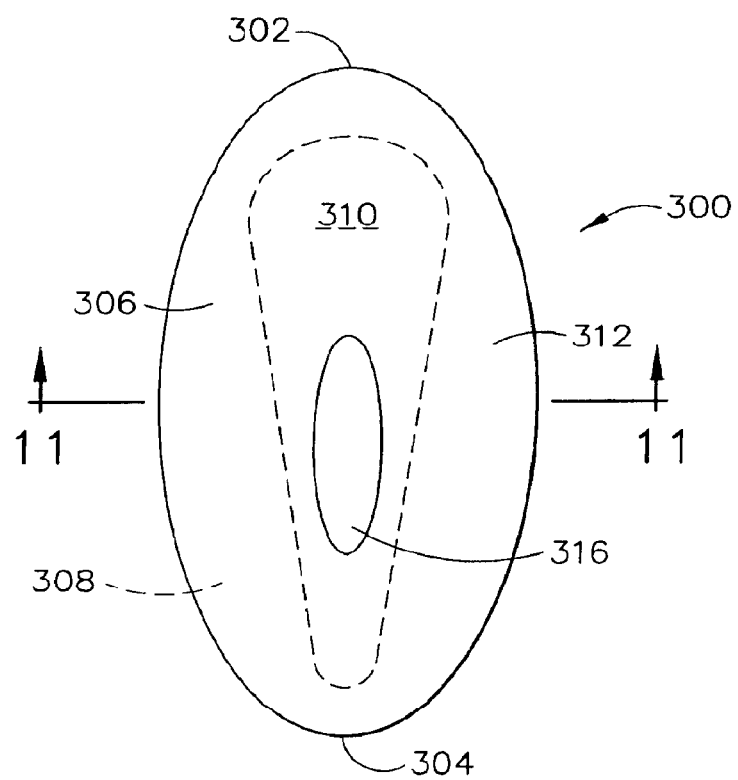
FIG. 10 is a plan view of the pad of FIG. 6 further comprising a longitudinal medial hump.
Figure 11:
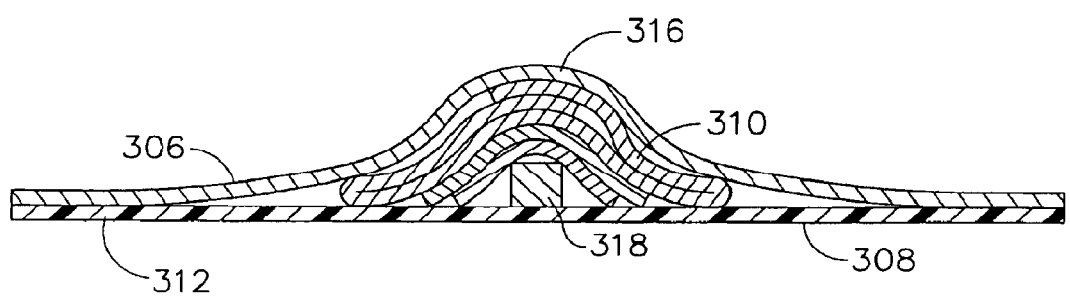
FIG. 11 is a sectional view of the pad of FIG. 10 taken along line 11-11.

FIGS. 10 and 11 illustrate the addition of such a longitudinal medial hump 316 on the body-contacting side of the pad 300 of FIG. 6. The pad comprises a liquid pervious, body-contacting side such as topsheet 306, a liquid impervious side such as backsheet 308 opposite the liquid pervious side, and an absorbent component such as absorbent core 310 between the liquid pervious side and the liquid impervious side. At least the liquid pervious side and the liquid impervious side of pad are arranged to form a unitary structure.

The hump 316 typically comprises a hump-forming element, such as hump core 318, that provides additional absorbent capacity and liquid acquisition capability in the target region of the pad. The hump also provides the sanitary pad with a centering/positioning mechanism. The hump typically maintains the sanitary pad in close physical contact with the wearer's body, particularly with the inwardly-contacting surfaces of the wearer's labia majora. The hump-forming element is typically a compressible and resilient material, and may comprise a material that is different from that in the absorbent core. The compressibility allows the hump, or at least its top half, to narrow and fit comfortably in the space between the wearer's labia. The resiliency allows the hump to better conform to the wearer's body and maintain such contact during wear. The hump-forming element is typically both wet and dry resilient. This provides the hump-forming element with resistance to collapsing under the conditions encountered during wear. The hump may comprise an absorbent foam material or synthetic fibers selected from the group consisting polyester fibers, synthetic fibers having capillary channels on their exteriors, polypropylene fibers, orlon fibers, fibrous absorbent gelling material, and mixtures thereof.

In another embodiment, such as described in U.S. Pat. No. 6,740,069, Drevik, the absorbent article has a substantially elongated shape with a longitudinal direction and a transverse direction with a hump extending in the longitudinal direction and having two longitudinally extending sides, and elastic members. The hump includes a formation element and the elastic members are arranged along either longitudinally extending side of the hump, wherein the formation element and the elastic members cooperate in shaping the hump.

In one embodiment, such as described in U.S. Pat. No. 6,316,688, Hammons, et al., the absorbent article has a three dimensionally-shaped tube of absorbent material extending outward from the body-contacting side of the article and aligned along its longitudinal centerline. The tube typically comprises an absorbent material and a cover at least partially wrapping the absorbent material. The tube typically comprises absorbent foam material or synthetic fibers selected from the group consisting polyester fibers, synthetic fibers having capillary channels on their exteriors, polypropylene fibers, orlon fibers, fibrous absorbent gelling material, and mixtures thereof.

Figure 12:
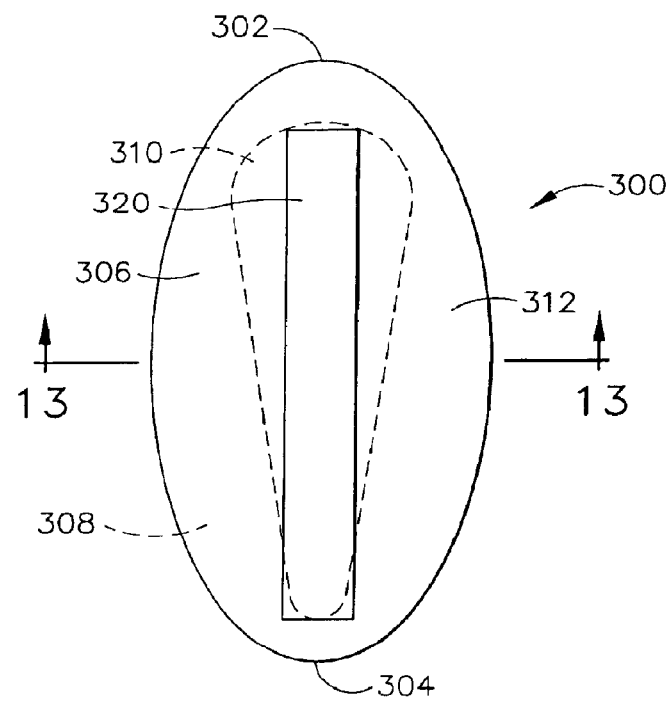
FIG. 12 is a plan view of the pad of FIG. 6 further comprising a longitudinal tube of absorbent material.
Figure 13:
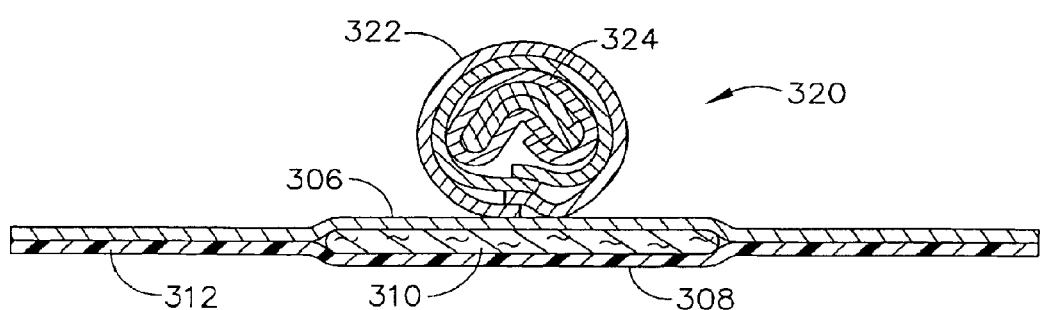
FIG. 13 is a sectional view of the pad of FIG. 12 taken along line 13-13.

FIGS. 12 and 13 illustrate the addition of such a three-dimensionally shaped tube 320 of absorbent material to the pad 300 of FIG. 6. The pad comprises a liquid pervious, body-contacting side such as topsheet 306, a liquid impervious side such as backsheet 308 opposite the liquid pervious side, and an absorbent component such as absorbent core 310 between the liquid pervious side and the liquid impervious side. The liquid pervious side and the liquid impervious side of pad 300 are arranged to form a unitary structure. The tube of absorbent material extends outward from the body-contacting side of the pad and is aligned along its longitudinal centerline. The tube comprises an absorbent material such as tube core 324 and a cover such as tube topsheet 322 at least partially wrapping the absorbent material.

Other absorbent articles useful herein include the interlabial insert devices described in U.S. Pat. No. 6,416,501, Brown, et al.; U.S. Pat. No. 6,355,022, Osborn III, et al.; U.S. Pat. No. 5,895,381, Osborn III, et al.; U.S. Pat. No. 5,484,429, Vukos, et al.; incorporated herein by reference. These interlabial devices perform even better when the holder of this invention assists in holding them in close bodily contact, with or without special body-adhesives.

Figure 15:
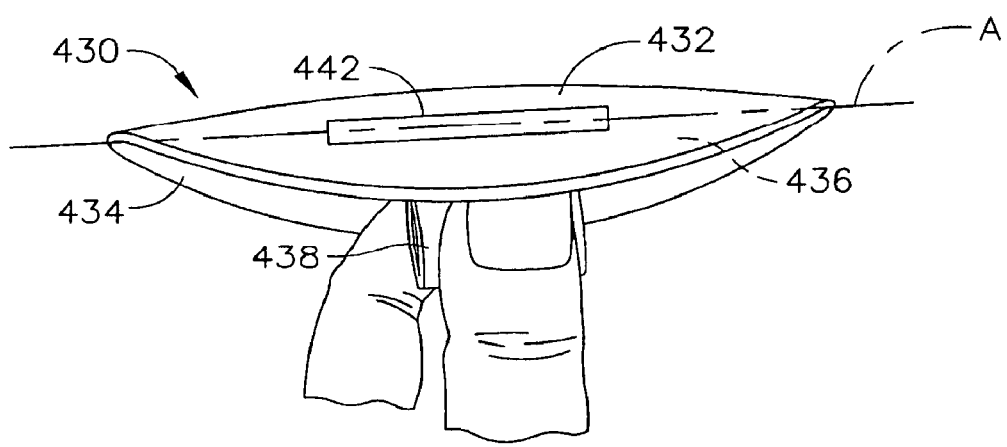
FIG. 15 is a perspective view of another interlabial device suitable for use with a holder herein.
Figure 17:
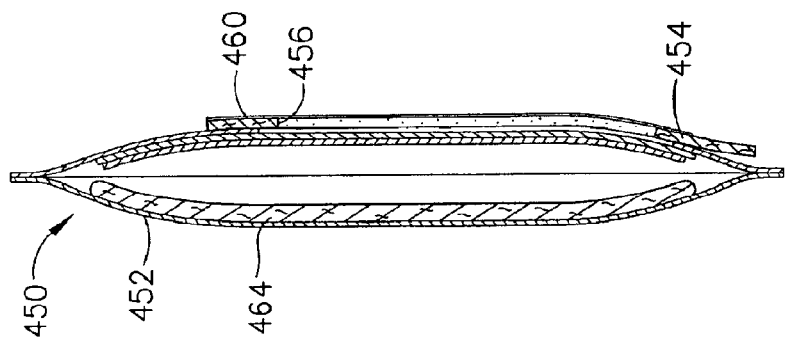
FIG. 17 is a sectional view of the device of FIG. 16 taken along line 17-17.
Figure 16:
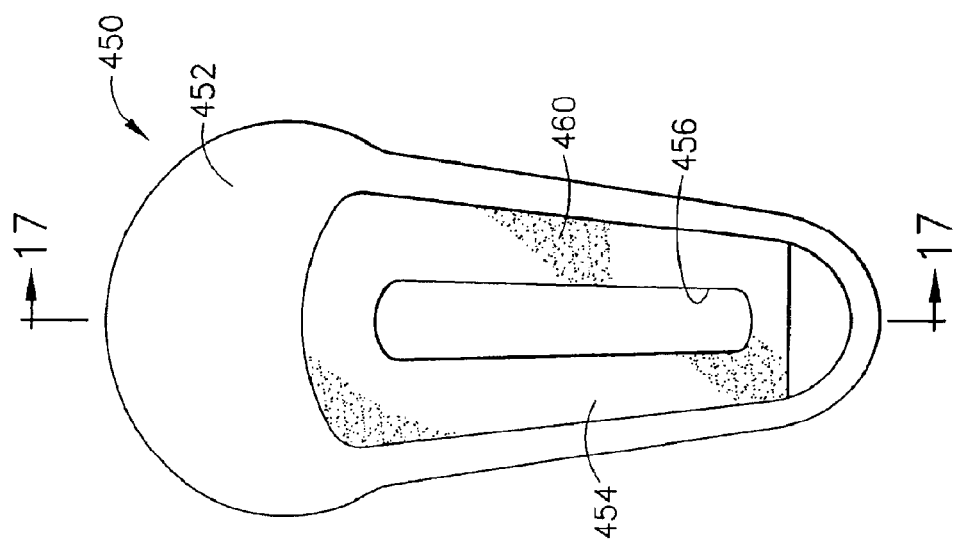
FIG. 16 is a plan view of an absorbent article fluid management device suitable for use with a holder herein.
Figure 18:
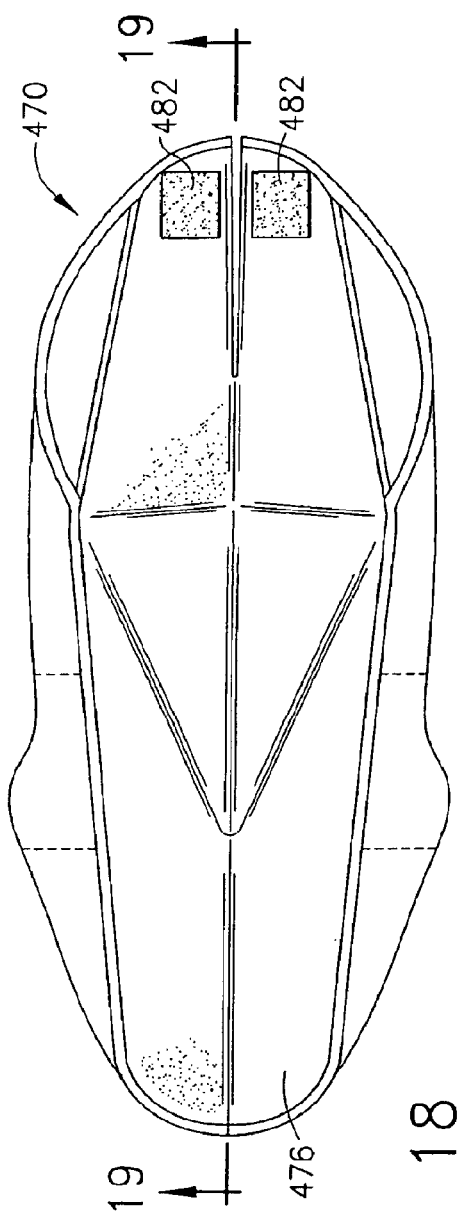
FIG. 18 is a plan view of an absorbent article designed to be applied directly to the user's body that is suitable for use with a holder herein.
Figure 19:
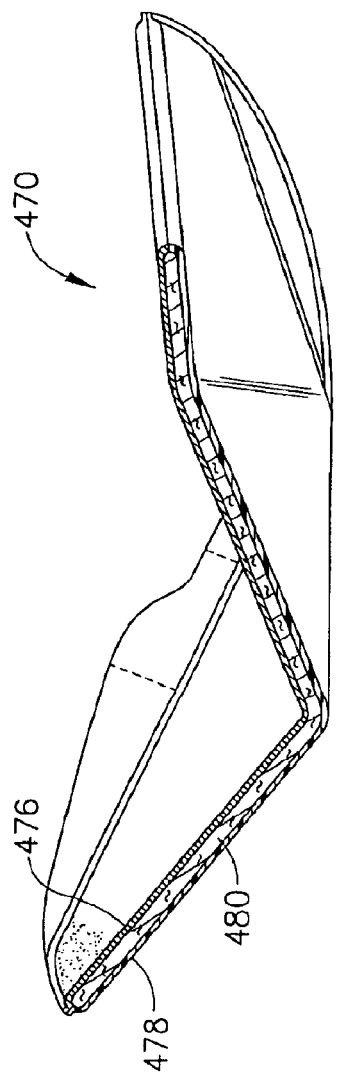
FIG. 19 is a sectional view of the article of FIG. 18 taken along line 19-19.

FIG. 15 illustrates an interlabial device 430 useful herein that is a small pad-like structure comprising a liquid pervious side such as topsheet 432, a liquid impervious side such as backsheet 434 joined to the topsheet, and an absorbent component such as absorbent core 436 positioned between the topsheet and backsheet. The liquid pervious side and the liquid impervious side are arranged to form a unitary structure. The length of the interlabial device typically is between about 60.0 mm and about 130.0 mm, and the width typically is between about 25.0 mm and about 40.0 mm. The device often comprises an axis of bending A such that when it is folded along the axis and inserted into the wearer's interlabial space, the liquid pervious topsheet side of the device maintains contact with the walls of the wearer's labia. Typically, the liquid pervious topsheet is constructed of rayon or needle punched rayon. The absorbent component typically comprises rayon, cotton, a superabsorbent polymer, or mixtures thereof. The device may also comprise a removal tab, such as removal tab 438, joined to the liquid impervious side of the device to facilitate insertion and removal of the device with the fingers.

In another embodiment, such as described in U.S. Pat. No. 6,355,022, Osborn III, et al., the interlabial device has at least one body-contacting surface, and comprises a non-adhesive substance having no initial tack on the body-contacting surface, wherein the non-adhesive substance is capable of contacting the inside of the wearer's labia to assist the device staying in position within the interlabial space. For example, the interlabial device 430 shown in FIG. 15 comprises such a non-adhesive substance 442. The non-adhesive substance typically has no initial tack so that it will not stick to the wrong portions of the wearer's body when the device is placed between the labia. Non-adhesive substances include moisture-activated substances that become viscous and develop a tack when contacted by relatively small amounts of moisture. In this embodiment, the substance adheres the interlabial device to the inside surfaces of the labia minora, or alternatively to the labia majora or both the labia minora and labia majora, so that it remains adhered to these surfaces (on both sides of the interlabial space) when the wearer moves in a way that the labia spread (e.g., when the wearer squats). This allows the interlabial device to remain in place during wearing conditions. The need for such a substance becomes more important as the loading that the interlabial device is expected to hold (that is, the weight of absorbed bodily liquids) increases. Typically, the unloaded interlabial device will weigh less than or equal to about 5.0 grams. As the weight of absorbed bodily liquids increases, the force of gravity on the loaded interlabial device increases. This results in the need for increased ability to hold the interlabial device in place, particularly when the exudate loading is greater than or equal to about 8.0 grams.

Moisture-activated substances are particularly useful with the interlabial device because they can make the device easier to apply. They are also particularly useful for sealing against this portion of the wearer's body since moisture is naturally present. Moisture-activated substances useful herein include polyethylene glycols ("PEGs"), sodium carboxymethylcellulose, cellulose gums, hydroxyethyl celluloses, hydroxypropyl celluloses, hydroxypropylmethyl celluloses, fanctionalized guars (such as cationic guar and hydroxypropyl guar), caffageenan, glycols (dihydric alcohols) such as propylene glycols, hexylene glycols, polyols which contain three or more hydroxyl groups such as glycerin, surfactants such as polyoxyl alkylates (polyoxyethylene sterates) ethoxylated alcohols, sugar surfactants, sugars (such as glucose, fructose, and sucrose), alone or in combination with pectin, guar gum, and other gums.

Figure 14:
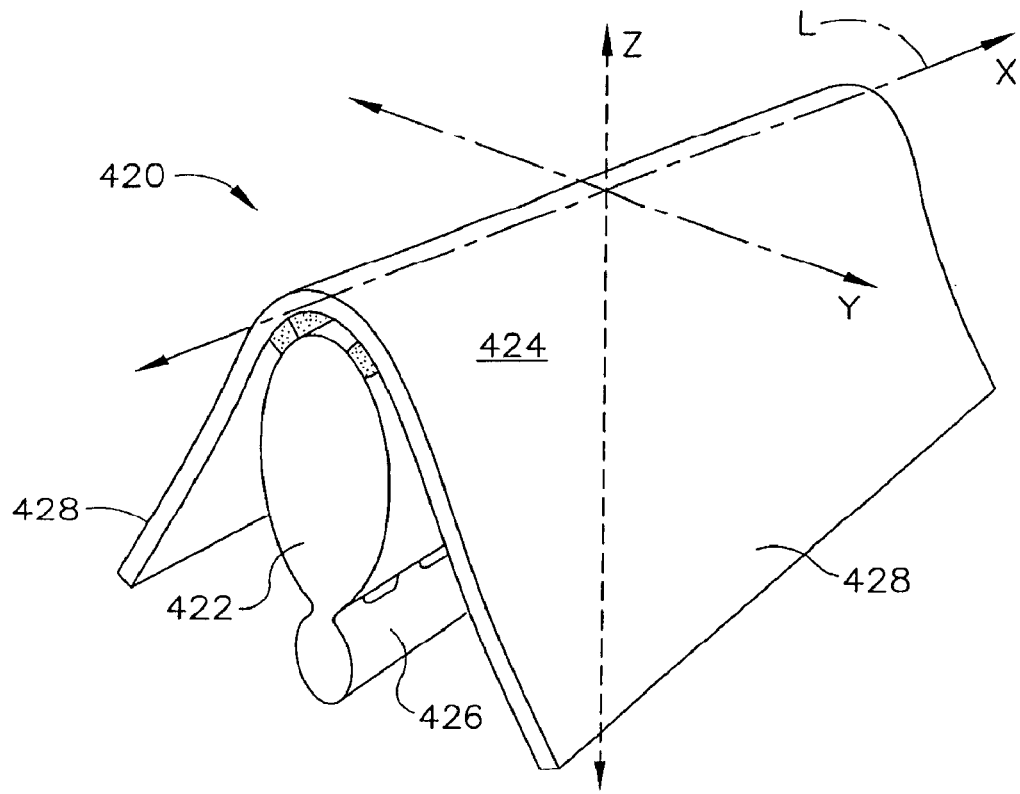
FIG. 14 is a perspective plan view of an interlabial device suitable for use with a holder of the invention.

Another interlabial device suitable for use herein is described in U.S. Pat. No. 5,895,381, Osborn III, et al. FIG. 14 illustrates such a device 420 comprising a liquid pervious side such as topsheet 424 and a liquid impervious side such as backsheet 426 that are arranged to form a unitary structure. The device often comprises an axis of bending X such that when it is folded along the axis and inserted into the wearer's interlabial space, the liquid pervious topsheet side of the device maintains contact with the walls of the wearer's labia. The device further comprises a pair of flexible extensions 428 joined to the absorbent component 422 and extending downwardly and outwardly therefrom, said flexible extensions being capable of contacting the inside surfaces of the wearer's labia when the device is worn. The flexible extensions block a direct "line of sight" from the outer perimeter of the labia majora to the vaginal introitus so that the flow of body exudates will be interrupted by the absorbent interlabial device. The holder of this invention assists in holding this interlabial device in close bodily contact. The performance of the interlabial device is further enhanced when the flexible extensions extend beyond the side elastics of the holder and serve as wings.

Another absorbent article useful herein may be referred to as a "pad-to-body" pad. Such articles are described in U.S. Pat. No. 6,746,436, Sierri, et al., incorporated herein by reference. For example, the sanitary pad 470 shown in FIGS. 18 and 19 comprises a liquid pervious side such as topsheet 476, a liquid impervious side such as backsheet 478 opposite the liquid pervious side, and an absorbent component such as absorbent core 480 between the liquid pervious side and the liquid impervious side. The liquid pervious side and the liquid impervious side are arranged to form a unitary structure. The pad 470 is designed to be applied directly to the user's body, and may comprise a fastening system such as skin-friendly adhesive 482 to adhere the article directly to the body. The absorbent article may be adapted to form a three dimensional shape before being applied directly to the user's body.

Other absorbent articles useful herein are described in U.S. Pat. No. 6,761,710, D'Acchioli, et al., U.S. Pat. No. 6,551,292 D'Acchioli, et al., and U.S. Pat. No. 6,508,794 Palumbo, et al., incorporated herein by reference. In one embodiment shown in FIGS. 16 and 17, the absorbent article is a disposable fluid management device 450, such as a menstrual fluid or a urine fluid management device, comprising a bag 452 having a flange 454 and an aperture 456. The bag typically comprises an adhesive layer 460 having a first surface and a second surface opposed thereto, wherein first surface is disposed proximate to the aperture and on an external surface of the bag, and the second surface is capable of providing releasable attachment of the bag to the uro-genital area of a wearer. The aperture typically is surrounded by an adhesively faced flange for releasable attachment to the uro-genital area of the wearer. These disposable fluid management devices are designed to acquire, absorb, and contain various exudates discharged from the body, including urine and menses. The bags are typically liquid impermeable. An absorbent material 464 may be disposed within the bags. The absorbent material may be selected from the group consisting of comminuted wood pulp; creped cellulose wadding; meltblown polymers; chemically stiffened, modified or cross-linked cellulosic fibers; tissue; absorbent foams; absorbent sponges; superabsorbent polymers; absorbent gelling materials; and mixtures thereof. The flange adhesive typically is selected from the group consisting of hydrogel adhesives, oilgel adhesives, hydrocolloid adhesives, and mixtures thereof.

Another article useful herein is the incontinence device described in U.S. Pat. No. 5,336,208, Rosenbluth, et al., incorporated herein by reference. The device is a urethral meatus occlusion device comprising a resilient body, configured to engage and seal against the urethral meatus and to be retained in place by engagement with the external female genitalia. In one embodiment, the body is a pad that includes a base having a substantially triangular or arrowhead-shaped outline that is adapted to seat against the vestibule of the vulva, anteriorly of the vaginal orifice, thereby occluding the urethral meatus. The lateral edges of the pad are configured to fit inside the labia minora. The engagement between the pad and the labia retains the pad against the vestibule in sealing engagement against the meatus. The article comprises a body of biocompatible material configured to fit between the labia minora and the vestibule floor, said body having surface means to occlude the urethral meatus. The surface has a vestibule floor-contacting surface on the body and an adhesive means on the vestibule floor-contacting surface for providing a sealing engagement between the body and the urethral meatus.

Figure 20:
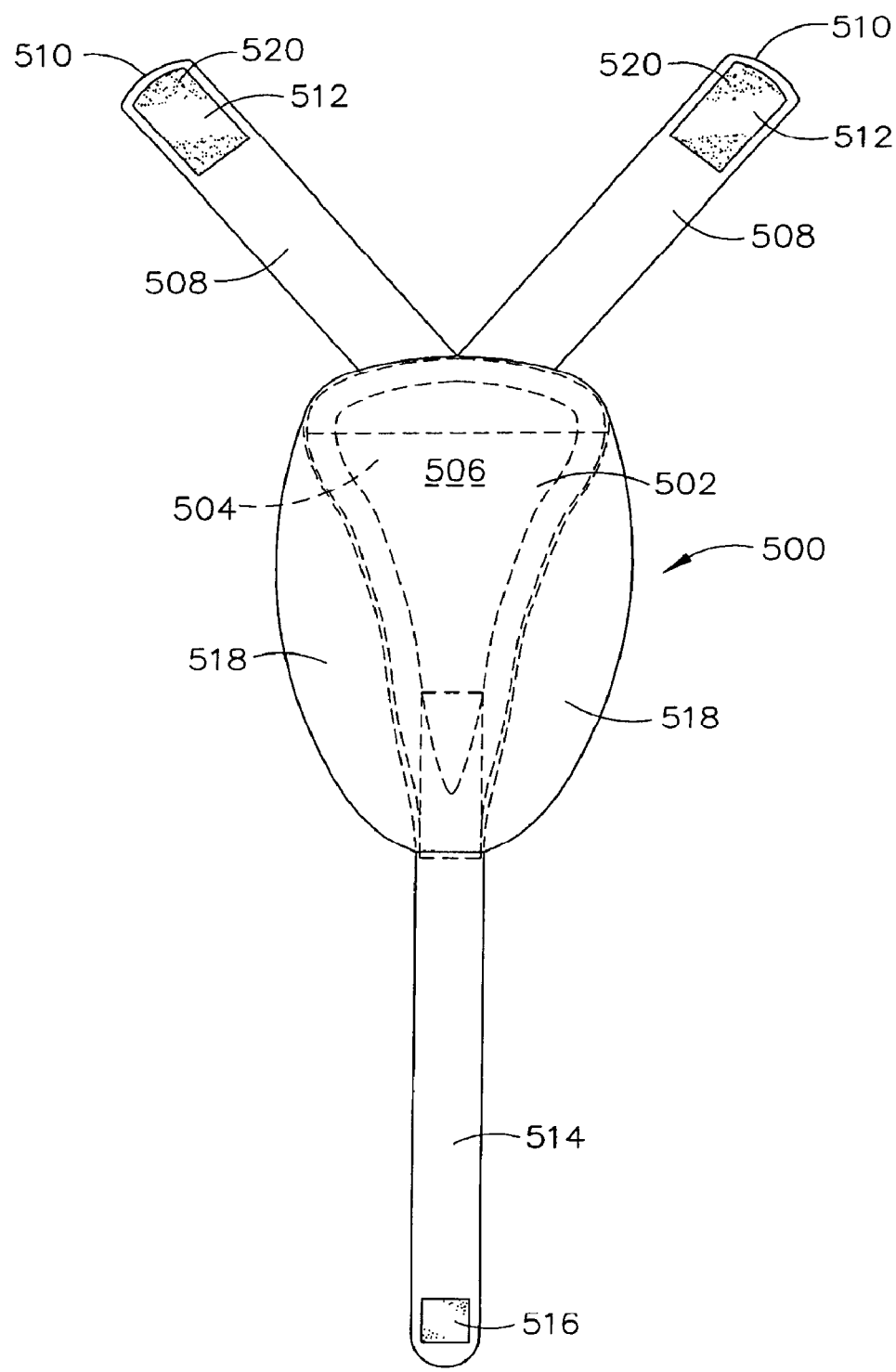
FIG. 20 is a plan view of another pad for use with a holder herein.
Figure 21:
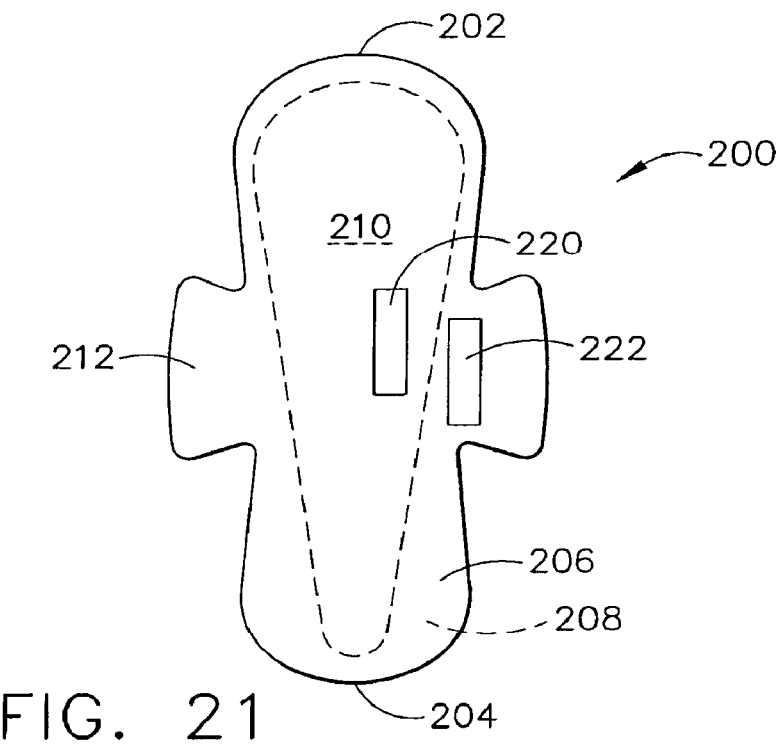
FIG. 21 is a plan view of the pad of FIG. 5 further comprising regions having compositions disposed thereon that are transferable to the wearer's skin.
Figure 22:
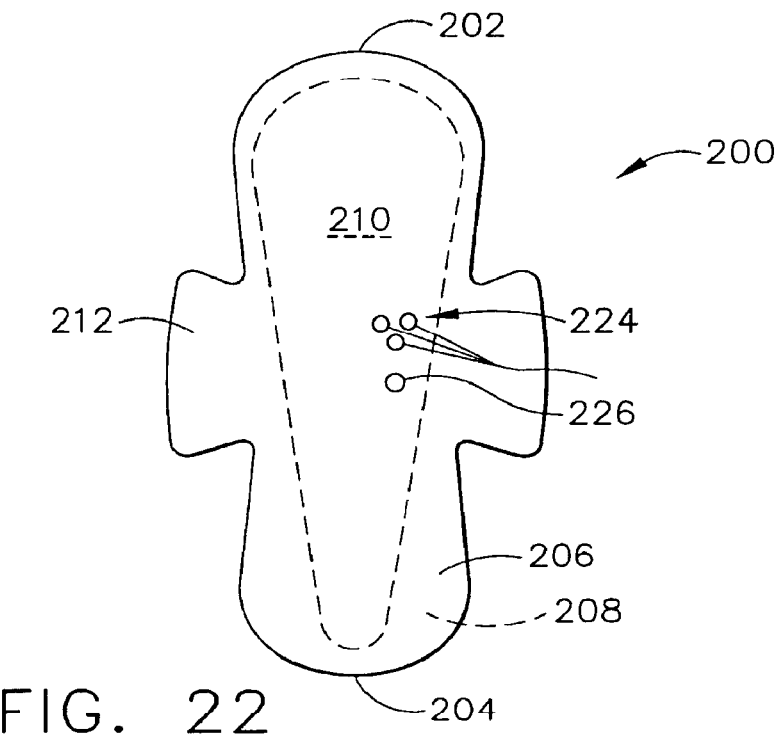
FIG. 22 is a plan view of the pad of FIG. 5 further comprising sensors operatively connected to the pad.

Other absorbent articles useful herein include the thong-shaped articles described in U.S. Pat. No. 6,632,210, Glasgow, et al.; U.S. Pat. No. 6,613,031, Glasgow, et al.; U.S. Pat. No. 6,629,965, Drevik, et al.; U.S. Pat. No. 6,554,812, Drevik; all incorporated herein by reference. The holder assists holding these articles in close bodily contact, and thus provides improved performance. In one embodiment, such as described in U.S. Pat. Nos. 6,632,210 and 6,613,031, the absorbent article is a pad that achieves a dynamic body fit adjacent to the wearer's vagina. The pad is closely fit to the user's body by means comprising an intergluteal strip. FIG. 20 shows such a sanitary pad 500 comprises a main pad body having an absorbent component such as absorbent core 506 positioned between a liquid pervious side such as topsheet 502 and a liquid impervious side such as backsheet 504, which are arranged to form a unitary structure. The absorbent core has a thong shape, and typically has a width less than or equal to the width of the crotch region of the holder. The pad comprises a rear end which in use is located in proximity to a wearer's buttocks and an opposed front end, a first face adapted to contact with the wearer's body and an opposing second face adapted to face toward the holder, and a main pad body thickness being defined as the dimension of the main pad body from the first face to the second face. The main pad body is adapted to be worn in close proximity to the vagina.

The pad 500 further comprises one or more flexible front flaps 508 extending forwardly from the front end of the pad and terminating at a distal end 510. The flaps are adapted to aid in retaining the article adjacent to the wearer's vagina. The distal ends of the front flaps comprise an area 512 adapted for attaching the distal end to the holder. The area 512 may comprise a fastening system such as described above. The front flaps may be extensible and may comprise a body adhesive 520 for attaching the front flaps to the wearer's body. The article further comprises a tail 514, which typically is relatively small in thickness compared to the absorbent article thickness. The tail extends rearwardly from the rear end of the pad, terminating at a distal end. The tail is configured to be received between the buttocks of the wearer to facilitate retaining the pad adjacent to the vagina. The tail may be extensible and may comprise an area 516 adapted to secure the tail to the holder or to the wearer's body, such as by using a fastening system as described above. In one embodiment, the thickness of the tail is between about 0.5 mm and about 10 mm; the width of the tail is between about 0.5 cm and about 2.5 cm; and the length of the tail is between about 10 and about 30 cm. The pad 500 further comprises wings 518 having a length at least about 75% of the length of the pad, typically at least about 85% of the length of the pad.

In another embodiment, such as described in U.S. Pat. No. 6,629,965, Drevik, et al., the absorbent article narrows rearwardly so it will fit effectively in the space between the wearer's buttocks and obtain good abutment with the wearer's body along its full length. Such fit provides an effective seal against rearward leakage. The absorbent article has a front portion and a rear portion, and an absorbent body enclosed between a liquid-permeable topsheet and a liquid-impermeable backsheet. The absorbent body comprises a central pad that extends from the front end of the front portion to the rear end of the rear portion, and two side bodies that extend along the side edges of the central absorbent body on respective sides thereof and along a part of the absorbent body. The central absorbent body narrows rearwardly from a section of greatest width in the front portion to the end of the rear portion. The side bodies extend rearwardly from a point on the tapering part of the central absorbent body that is located in the front part of the rear end of the article. Because the central absorbent body tapers or narrows rearwardly, it will fit effectively in the space between the wearer's buttocks and obtain good abutment with the wearer's body along its full length. This provides an effective seal against rearward leakage. The side bodies lie against the wearer's buttocks and therewith ensure an effective seal against lateral leakage at the rear portion of the article.

Figure 23:
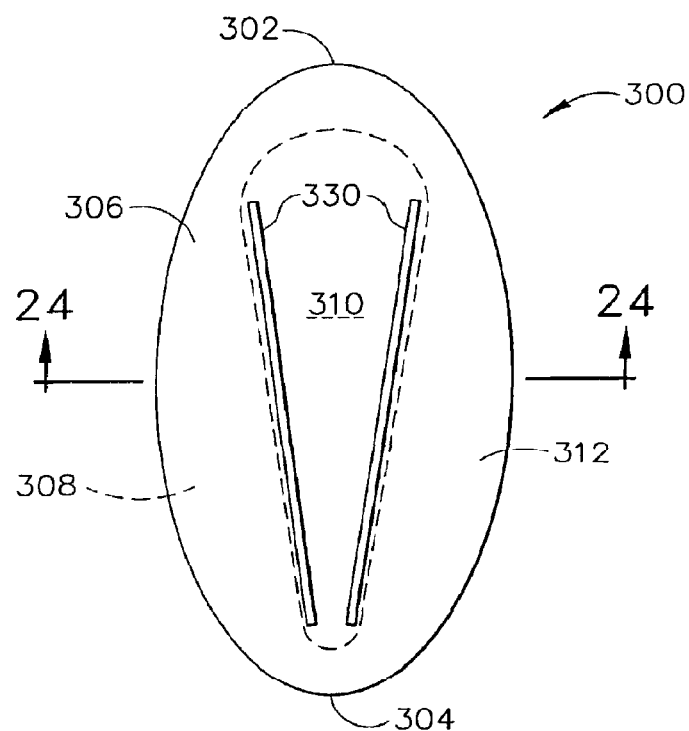
FIG. 23 is a plan view of the pad of FIG. 6 further comprising a pair of side shields.
Figure 24:
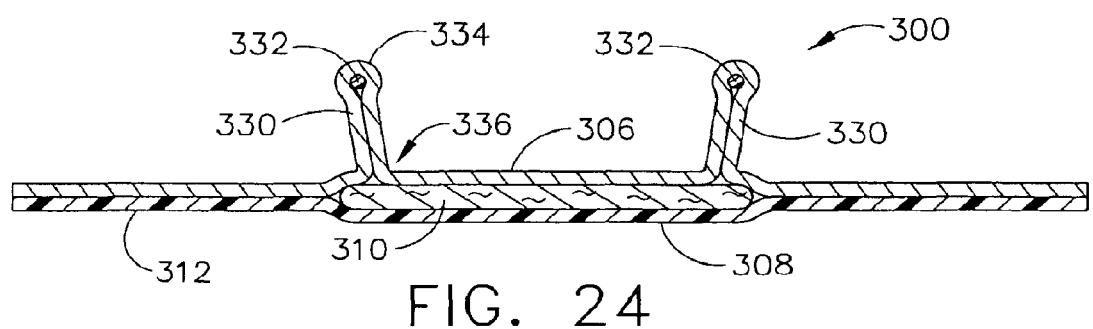
FIG. 24 is a sectional view of the pad of FIG. 23 taken along line 24-24.

Another article useful herein comprises elasticized side shields, such as described in U.S. Pat. No. 6,773,424, Heyrman, et al., incorporated herein by reference. In one embodiment shown in FIGS. 23 and 24, a pair of side shields 330 are formed on opposite sides of the sanitary pad of FIG. 6 by a first elastic member 332 adjacent the first side of the pad and a second elastic member 332 adjacent the second side of the pad, the first and second elastic members contracting at least a portion of the first and second sides. Each of the side shields has an upstanding end 334 and a terminal end 336 adjacent the absorbent core 310 of the pad. The side shields may be formed by an extension of the topsheet, such topsheet 306 as shown in FIG. 24, in which event the side shields would typically be glued along their terminal ends 336. Alternatively, the side shields may be formed as separate elements that are attached to the topsheet, such as by gluing them to the topsheet. The side shields may extend the entire length of the pad or they may be shorter such as shown in FIG. 23, in which event they typically would be formed as separate elements that are attached to the topsheet. The holding force provided by the crotch region of the holder herein combined with the fit within the low motion zone enhances the close body fit of the pad with such elasticized side shields. The close body fit and low relative motion improves urine side leakage protection versus that typically provided using conventional undergarments.

In one embodiment, articles useful herein comprise a lotion coating, a skin care composition, or a therapeutic composition that is at least partially transferable to the wearer's skin, such as described in U.S. Pat. No. 6,290,979, Roe, et al.; U.S. Pat. No. 6,156,024, Schulte, et al.; U.S. Pat. No. 5,609,587, Roe; U.S. Pat. No. 5,607,760, Roe; all incorporated herein by reference. The holder maintains the article comprising the lotion, skin care composition or therapeutic composition in close bodily contact in the pudendal region and within the low-motion zone of the body, and thus provides improved transfer of the lotion, skin care composition or therapeutic composition to the skin. The article may comprise one or more absorbent components or may be void of any absorbent component. The article has a body-contacting surface such as the topsheet described above and a holder-contacting surface such as the backsheet described above, although in this article the topsheet need not be liquid pervious and the backsheet need not be liquid impervious. The lotion, skin care composition, or therapeutic composition is transferable to the wearer's skin in an effective amount to provide a skin health benefit or other therapeutic or health benefit.

One embodiment, such as described in U.S. Pat. No. 5,607,760, Roe, relates to an article having a lotion coating on the outer surface oriented toward the skin of the wearer, wherein at least a portion of the body-contacting surface of the article comprises a lotion coating which is solid or semi-solid at 20° C. and which is partially transferable to the wearer's skin. The lotion typically comprises: (i) from about 5 to about 95% of a substantially water free emollient having a plastic or fluid consistency at 20° C. and comprising a member selected from the group consisting of petroleum based emollients, fatty acid ester emollients, alkyl ethoxylate emollients, polysiloxane emollients, silicone wax emollients, and mixtures thereof; (ii) from about 5% to about 95% of an agent capable of immobilizing said emollient on the outer surface of the body-contacting surface, said immobilizing agent having a melting point of at least 35° C. and comprising a solid polyol polyester comprising a polyhydric alcohol containing at least 4 hydroxyl groups esterified with fatty acid or other organic radicals having from about 2 to about 30 carbon atoms. The quantity of lotion coating on at least a portion of the body-contacting surface typically ranges from about 0.1 mg/in$^2$ to about 25 mg/in$^2$, more typically from about 1 mg/in$^2$ to about 10 mg/in$^2$. Such lotioned articles provide therapeutic and/or protective lotion coating benefits. Because the emollient is substantially immobilized on the surface of the article, less lotion composition is needed to impart the desired benefits. Importantly, the lotion is easily transferable to the skin by way of normal contact, wearer motion, and/or body heat.

Another embodiment, such as described in U.S. Pat. No. 6,290,979, Roe et al., relates to an article having two or more skin care compositions disposed thereon. The skin care compositions, such as the lotions described above, may have different formulations such that the article can be designed to deliver specific skin care benefits to specific portions of the skin of the user. In one embodiment shown in FIG. 21, the sanitary pad of FIG. 5 further comprises a first region such as region 220 and a second region such as region 222. The first region has a first skin care composition disposed thereon that is semi-solid or solid at 20° C. and partially transferable to a wearer's skin. The second region has a second skin care composition disposed thereon that is semi-solid or solid at 20° C. and partially transferable to a wearer's skin. The first skin care composition has a different formulation than the second skin care composition. The first skin care composition is disposed in an effective amount to provide a first skin health benefit and the second skin care composition is disposed in an effective amount to provide a second skin health benefit. Alternatively, regions 220 and 222 may comprise the same or different lotions, skin care compositions, or therapeutic compositions, which are at least partially transferable to the wearer's skin.

The holder of this invention can also be used with an article capable of being held in close bodily contact in the pudendal region by the holder, and comprising a sensor that is operatively connected to the article. The sensor is capable of detecting various target entities, including inputs that correlate to elimination of bodily wastes, biological analytes, etc., such as described in U.S. Pat. No. 6,570,053, Roe, et al.; and U.S. Pat. No. 6,713,660, Roe, et al.; both incorporated herein by reference. The holder maintains the article in close bodily contact in the pudendal region and within the low-motion zone of the body, and thus provides improved sensor performance.

One embodiment, such as described in U.S. Pat. No. 6,570,053, Roe, et al., relates to an article that predicts the occurrence of an event related to bodily waste, the wearer, the article, or a component or components thereof using a proactive sensor, and responds to this prediction by performing a function on the article or the wearer to prepare for or to delay the occurrence of the predicted event, or by signaling the caretaker or the wearer that the event is about to occur. Such a sensor could also signal that an event has occurred. The article typically comprises a sensor operatively connected to the article, the sensor being capable of detecting an input that correlates to elimination of bodily waste from the wearer; and means for signaling elimination of bodily waste. In one embodiment shown in FIG. 22, the sanitary pad of FIG. 5 further comprises such a sensor 224. The sensor may be integral with or separate from the article. The elimination of bodily waste may include urination, discharge of menses, or defecation. The input may be a change in pressure, an electrical signal, or a motion, or combinations thereof The article may or may not be disposable, and may or may not comprise an absorbent component.

Another embodiment, such as described in U.S. Pat. No. 6,713,660, Roe, et al, relates to an article that comprises a biosensor including at least one bio-recognition element and a transducer. The bio sensor is adapted to detect a target biological analyte in bodily waste or on the wearer's skin. The article may comprise a biosensor adapted to detect one or more specific microorganisms and/or related biomolecules and to signal the caretaker, the wearer, or an actuator of the occurrence. The bio-recognition element may comprise a biologically reactive agent, typically selected from the groups consisting of an enzyme or sequence of enzymes; an antibody; DNA; an organelle; a membrane receptor protein; a natural or synthetic cell membrane; viable or nonviable bacterial, plant, or animal cells; at least a portion of a nerve bundle; and at least a portion of a sensing organ; and combinations thereof. The bio-recognition element may be *Acinetobacter baumannii* TOI36 and *Bacillus* sp TOI41. The biosensor is typically a biocatalytic biosensor or a bioaffinity biosensor. The bioaffinity biosensor may be a chemoreceptor-based biosensor and an immunosensor. The biosensor may detect target biological analytes selected from the group consisting of pathogenic bacteria, colonic bacteria, viruses, parasites, bacterial toxins, fungi, enzymes, and combinations thereof. The biosensor may also detect target biological analytes associated with a systemic or skin health condition in the wearer prior to the onset of clinically observable symptoms of the condition. The biosensor typically detects the target biological analyte only above a pre-defined threshold level. In one embodiment shown in FIG. 22, the sanitary pad of FIG. 5 further comprises such a biosensor 226. The article may or may not be disposable, and may or may not comprise an absorbent component.

Test Method for Measuring the Crotch Holding Force (CHF) of a Material Using A "Constant-Rate-of-Extension (CRE) Ball Force Test"

Overview: This method measures a force (CHF) that is related to the holding force exerted by an extensible material when holding an article against a wearer's body.

Terminology: The Crotch Holding Force (CHF) is the force exerted by a material when distending it with a force applied at right angles to the plane of the material, under the specified conditions. The angle of application of force and the area of the material upon which the force is applied varies continuously as the material stretches when tested as directed in this method. In the Constant-Rate-of-Extension (CRE) tensile testing machine, the rate of increase of the specimen length is uniform with time.

Summary of Test Method: Set up the tensile testing machine for performing this test in accordance with both the manufacture's instructions and procedures presented herein. A specimen of material is securely clamped without tension within a "Ball Burst Test" attachment. A force is exerted against the specimen by a polished, hardened steel ball attached to the tensile testing machine. Crotch Holding Force (CHF) data are recorded as a function of extension distance.

Apparatus: Tensile testing machine, of the constant-rate-of-extension (CRE) type. Equipment includes an Imada DPZ High Performance Programmable Digital Force Gauge: Model DPZ-4, and an Imada Motorized Vertical Test Stand: Model MX-110-S Test Stand w/Digital Distance Meter, both available from Imada, Incorporated, Northbrook, Ill. The Force Ball Attachment (a modified "Ball Burst Test" attachment) consists of a clamping mechanism to hold the specimen and a steel ball attached to the moveable force gauge of the tensile testing machine. The circular opening and ring clamp have an internal diameter of 5.1 cm (2.0 in). The polished steel ball connected to the force gauge has a diameter of 1.6 cm (0.62 in).

Sampling and Specimen Preparation: The specimen is taken from the crotch region of the holder. Clamp the specimen in the ring clamp of the apparatus. The specimen must be of sufficient diameter to be held securely within the 5.1 cm (2.0 in) diameter ring clamp. The specimen may not require cutting if there is ample room to securely clamp the specimen in the apparatus. Ensure the specimen is free of folds, creases, or wrinkles, and is without tension when clamped. If the specimen is not uniform (e.g., it has a pattern, stitching, or a seam, etc.), ensure that the area tested is representative of the crotch region.

Procedure:

Place the specimen in the ring clamp, without tension, and fasten securely.

Move the Force Ball to a position immediately adjacent the specimen. Make sure there is no force applied to the ball by the specimen (CHF-0.0=0 kgf).

Set the distance meter to zero (0 cm elongation).

Start the CRE machine and maintain a speed of 25.4+/−10 cm/min (10.0+/−0.5 in/min). Continue that speed until the specimen is extended at least 6.5 cm (2.6 in) or until a force of at least 2.0 kgf (4.5 lbf) is reached.

While the CRE machine and Force Ball are elongating the specimen, record Crotch Holding Force and elongation data at 0.5 second intervals.

Create a standard stress/strain curve (Crotch Holding Force versus elongation distance) with the resulting data.

Determine Crotch Holding Force (CHF) at the appropriate elongation distances.

In the above method:

CHF-0.0 is the force at 0 cm specimen elongation, i.e., the start of data collection. CHF-0.0 should be 0 kgf at 0 cm elongation.

CHF-2.0 is the force (kgf) at 2.0 cm Force Ball extension distance.

CHF-4.0 is the force (kgf) at 4.0 cm Force Ball extension distance.

CHF-5.5 is the force (kgf) at 5.5 cm Force Ball extension distance.

CHF-6.5 is the force (kgf) at 6.5 cm Force Ball extension distance.

Test Method for Measuring the Elastic Holding Force (EHF) of a Material Using A "Constant-Rate-of-Extension (CRE) Force Test"

Overview: This method measures a force (EHF) that is related to the elastic force exerted by an extensible side elastic material attached to an extensible material.

Terminology: The Elastic Holding Force (EHF) is the force exerted by a material when distending it with a force applied at right angles to the plane of the material, under the specified conditions. The angle of application of force and the area of the material upon which the force is applied varies continuously as the material stretches when it is tested as directed in this method. In the Constant-Rate-of-Extension (CRE) tensile testing machine, the rate of increase of the specimen length is uniform with time.

Summary of Test Method: Set up the tensile testing machine for performing this test in accordance with both the manufacture's instructions and procedures presented herein. A specimen of material is securely clamped without tension within a "Ball Burst Test" attachment. A force is exerted against the specimen by a polished, hardened steel cylinder attached to the tensile testing machine. Elastic Holding Force (EHF) data are recorded as a function of extension distance Apparatus: Tensile testing machine, of the constant-rate-of-extension (CRE) type. Equipment includes an Imada DPZ High Performance Programmable Digital Force Gauge:

Model DPZ-4 and an Imada Motorized Vertical Test Stand: Model MX-110-S Test Stand w/Digital Distance Meter, both available from Imada, Incorporated, Northbrook, Ill. The Force Cylinder Attachment (a modified "Ball Burst Test" attachment) consists of a clamping mechanism to hold the specimen and a steel cylinder attached to the moveable force gauge of the tensile testing machine. The circular opening and ring clamp have an internal diameter of 5.1 cm (2.0 in). The polished steel cylinder connected to the force gauge has a diameter of 1.6 cm (0.62 in) and a length of 1.6 cm (0.62 in).

Sampling and Specimen Preparation: The specimen is cut from the side elastic attached to the crotch region of the holder. The side elastic to be tested extends from the lateral centerline of the holder to 5.1 cm (2.0 in) above the lateral centerline. The specimen must be of sufficient length to be held securely within the 5.1 cm (2.0 in) diameter ring clamp. The specimen must retain about 0.5 cm (0.2 in) of the crotch region material along the entire length of the specimen. Position the specimen perpendicular to the steel cylinder's longitudinal axis and clamp it securely in the ring clamp. Ensure the specimen is without tension when clamped.

Procedure:

Place the specimen in the ring clamp, without tension, perpendicular to the steel cylinder's longitudinal axis, and fasten securely.

Move the Force Cylinder to a position immediately adjacent the specimen. Make sure there is no force applied to the cylinder by the specimen (EHF-0.0=0 kgf).

Set the distance meter to zero (0 cm elongation).

Start the CRE machine and maintain a speed of 12.7+/−10 cm/min (5.0–0.5 in/min). Continue that speed until the specimen is extended at least 6.4 cm (2.5 in) or until a force of at least 2.0 kgf (4.5 lbf) is reached.

While the CRE machine and Force Cylinder are elongating the specimen, record Elastic Holding Force and elongation data at 0.5 second intervals.

Create a standard stress/strain curve (Elastic Holding Force versus elongation distance) with the resulting data.

Determine Elastic Holding Force (EHF) at the appropriate elongation distances.

In the above method:

EHF-0.0 is the force at 0 cm specimen elongation, i.e., the start of data collection. EHF-0.0 should be 0 kgf at 0 cm elongation.

EHF-4.5 is the force (kgf) at 4.5 cm Force Cylinder extension distance.

EHF-5.5 is the force (kgf) at 5.5 cm Force Cylinder extension distance.

Test Method for Measuring Caliper

A comparator gauge such as the Ames, Model 130 with dial indicator Model 482, available from the B. C. Ames, Company of Waltham, Mass. is needed. The comparator gauge should typically have a circular comparator foot, a weight of 10.0 grams and a contact surface of 5.16 square centimeters. The gauge is further provided with an 80.0 gram weight to provide a total of 0.25 psi pressure. The comparator gauge is zeroed. The weight is placed on the spindle extending above the comparator dial. The comparator foot is raised and the absorbent article, with any adhesive release paper being removed and the adhesive sprinkled with corn starch, is placed garment surface down on the base plate. The absorbent article is positioned on the base plate so that when the foot is lowered, it is in the region of the article for which the measurement is desired. Try to smooth out or avoid any wrinkles. Gently lower the foot onto the absorbent article. Determine the caliper by reading the comparator dial 30 seconds after the foot comes in contact with the surface.

Test Method for Measuring Flexure-Resistance

The flexure-resistance of the absorbent article is measured as peak bending stiffness. Peak bending stiffness is determined by a test which is modeled after the ASTM D 4032-82 Circular Bend Procedure. The ASTM procedure is modified for use herein. The Circular Bend Procedure as modified and used for the purposes of the present invention is hereinafter simply referred to as the "Circular Bend Procedure". One version of the Circular Bend Procedure is described in U.S. Pat. No. 5,009,653 issued to Osborn. The Circular Bend Procedure is a simultaneous multi-directional deformation of a material in which one face of a specimen becomes concave and the other face becomes convex. The Circular Bend Procedure gives a force value related to flexure-resistance, simultaneously averaging stiffness in all directions.

Apparatus: The apparatus necessary for the Circular Bend Procedure is a modified Circular Bend Stiffness Tester, having the following parts: A smooth-polished steel plate platform which is 102.0 by 102.0 by 6.35 millimeters having an 18.75 millimeter diameter orifice. The lap edge of the orifice should be at a 45 degree angle to a depth of 4.75 millimeters. A plunger having an overall length of 72.2 millimeters, a diameter of 6.5 millimeters, a ball nose having a radius of 2.97 millimeters and a needle-point extending 0.88 millimeter therefrom having a 0.33 millimeter base diameter and a point having a radius of less than 0.5 millimeter, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), then the needle-point should not be used. The bottom of the plunger should be set well above the top of the orifice plate. From this position, the downward stroke of the ball nose is to the exact bottom of the plate orifice. A force-measurement gauge and more specifically an Instron inverted compression load cell. The load cell has a load range of from about 0.0 to about 2000.0 grams. An actuator, and more specifically the Instron Model No. 1122 having an inverted compression load cell. The Instron 1122 is made by the Instron Engineering Corporation, Canton, Mass.

Number and Preparation of Specimens: In order to perform the procedure for this test, as explained below, five representative absorbent articles are necessary. From one of the five articles to be tested, some number "Y" of 37.5 by 37.5 millimeter test specimens are cut. If due to the plan view shape of the region to be tested, it is not possible to cut a square 37.5 by 37.5 mm. specimen, any other 1,400 square millimeter size specimen may be used, provided the specimen adequately covers the orifice in the test platform to properly carry out the test. If any of the significant absorbent portions of the absorbent article meet the parameters set forth in the appended claims for the particular regions, then the absorbent article falls within the scope of the appended claims. A number of different specimens should be tested from each absorbent article. In particular, the structurally least flexible portions in the center of the absorbent article should be tested as the longitudinal central region. The most flexible portions of the absorbent article should be tested when samples of the surrounding regions of the article are measured. The test specimens should not be folded, bent, or compressed by the test person, and the handling of specimens must be kept to a minimum and to the edges to avoid affecting flexural-resistance properties. From the four remaining absorbent articles, an equal number "Y" of specimens, identical to the specimens cut from the first article, are cut. Thus, the test person should have "Y" number of sets of five identical specimens.

Procedure: The procedure for the Circular Bend Procedure is as follows. The specimens are conditioned by leaving them in a room at a temperature of 21+/−1° C. and 50+/−2% relative humidity for a period of two hours. The test plate is leveled. The plunger speed is set at 50.0 centimeters per minute per full stroke length. A specimen is centered on the orifice platform below the plunger such that the body surface of the specimen is facing the plunger and the garment surface of the specimen is facing the platform with the release paper removed from any adhesive on the garment surface of the specimen and the adhesive sprinkled with corn starch to eliminate the adhesive tack. The indicator zero is checked and adjusted, if necessary. The plunger is actuated. Touching the specimen during the testing should be avoided. The maximum force reading to the nearest gram is recorded. The above steps are repeated until all five of the identical specimens have been tested.

Calculations: The peak bending stiffness for each specimen is the maximum force reading for that specimen. Each set of five identical specimens is tested and the five values received for that set are averaged. Thus, the test person now has an average value for each of the "Y" identical sets of specimens tested.

Test Method for Measuring Absorbent Capacity

The capacity of an absorbent article is determined as follows. Any panty adhesive release paper is removed from the article to be tested. To determine absorbent capacity, a sample comprising the entire article minus any release paper is obtained. The sample is weighed to the nearest 0.1 gram. The sample is then submerged in a beaker of 1% sterile saline (obtainable from the Baxter Travenol Company of Deerfield, Ill.), such that the sample is totally submerged and is not bent or otherwise twisted or folded. The sample is submerged for 10 minutes. The sample is removed from the saline and suspended for two minutes in a vertical position to allow the saline to drain out of the sample. The sample is then placed body-contacting surface down onto an absorbent blotter, such as the filter paper #631 available from the Filtration Science Corp., Eaton-Dikeman Division of Mount Holly Springs, Pa. A uniform 17.6 gram per square centimeter load is placed over the sample to squeeze excess fluid out. The absorbent blotter is replaced every 30 seconds until the amount of fluid transferred to the absorbent blotter is less than 0.5 grams in a 30 second period. Next, the sample is weighed to the nearest 0.1 gram and the dry weight of the sample is subtracted. The difference in grams is the absorbent capacity of the article.

All limits and ranges specified herein include all narrower ranges, limits, and amounts that are within the specified limits and ranges, and such narrower ranges and limits may be claimed even though those limits and ranges are not separately listed.

While particular embodiments of the present invention have been illustrated and described, various other changes and modifications can be made without departing from the spirit and scope of the invention. It is therefore intended to cover all such changes and modifications that are within the scope of this invention.

What is claimed is:

1. A system comprising:
    a) a thong-shaped holder for holding an absorbent article in close bodily contact in the pudendal region, said holder having a longitudinal centerline defining a longitudinal direction and a lateral centerline defining a lateral direction, said holder comprising:
        1) a front region;
        2) a crotch region attached to the front region, said crotch region comprising elastic nonwoven material suitable for use in an undergarment, said crotch region having high stretch in both the lateral and longitudinal directions as measured by having a Crotch Holding Force (CHF-4.0) of greater than about 0.1 kgf and a Crotch Holding Force (CHF-2.0) of less than about 1.0 kgf; and
        3) a rear region attached to the front and crotch regions and cooperating with the front region to provide an adjustable waistband; and
    b) an absorbent article capable of being held in close bodily contact in the pudendal region by said thong-shaped holder.

2. A system according to claim 1 wherein the absorbent article comprises a primary absorbent core that has a width less than or equal to the width of the crotch region of the holder.

3. A system according to claim 2 wherein the primary absorbent core has a thong shape.

4. A system according to claim 1 wherein the absorbent article comprises wings.

5. A system according to claim 1 wherein the absorbent article comprises wings having a length at least about 75% of the length of the absorbent article.

6. A system according to claim 1 wherein the crotch region of the holder has a Crotch Holding Force (CHF-2.0) of less than about 0.6 kgf.

7. A system according to claim 1 wherein the crotch region of the holder has a Crotch Holding Force (CHF-4.0) of less than about 1.0 kgf.

8. A system according to claim 1 wherein the crotch region of the holder has a Crotch Holding Force (CHF-5.5) of less than about 1.0 kgf.

9. A system according to claim 1 wherein the crotch region of the holder has a width measured 10.0 cm above the lateral centerline of from about 6.0 to about 15.0 cm, and a width at the lateral centerline of from about 1.5 to about 10.0 cm.

10. A system according to claim 1 wherein the holder further comprises side elastics.

11. A system according to claim 1 wherein the holder comprises at least one extension or panel extending beyond the front, crotch, or rear region.

12. A system according to claim 1 wherein the absorbent article comprises an absorbent core that comprises absorbent foam material.

13. A system comprising:
    a) a thong-shaped holder for holding an absorbent article in close bodily contact in the pudendal region, said holder having a longitudinal centerline defining a longitudinal direction and a lateral centerline defining a lateral direction, said holder comprising:
        1) a front region;
        2) a crotch region attached to the front region, said crotch region comprising elastic nonwoven material suitable for use in an undergarment, said crotch region having high stretch in both the lateral and longitudinal directions as measured by having a Crotch Holding Force (CHF-4.0) of greater than about 0.1 kgf and a Crotch Holding Force (CHF-2.0) of less than about 1.0 kgf;
        3) a rear region attached to the front and crotch regions and cooperating with the front region to provide an adjustable waistband; and
        4) side elastics in the crotch region; and
    b) an absorbent article capable of being held in close bodily contact in the pudendal region by said thong-shaped holder, said absorbent article comprising a primary absorbent core that has a thong shape and a width that is less than or equal to the width of the crotch region of the holder, and comprising wings having a length at least about 75% of the length of the absorbent article.

14. A system according to claim 13 wherein the crotch region of the holder has a Crotch Holding Force (CHF-2.0) of less than about 0.6 kgf.

15. A system according to claim 13 wherein the crotch region of the holder has a Crotch Holding Force (CHF-4.0) of less than about 1.0 kgf.

16. A system according to claim 13 wherein the side elastics in the crotch region of the holder have an Elastic Holding Force (EHF-4.5) of less than about 0.8 kgf.

17. A system comprising:
    a) a thong-shaped holder for holding an absorbent article in close bodily contact in the pudendal region, said holder having a longitudinal centerline defining a longitudinal direction and a lateral centerline defining a lateral direction, said holder comprising:
        1) a front region;
        2) a crotch region attached to the front region, said crotch region comprising elastic nonwoven material suitable for use in an undergarment, said crotch region having high stretch in both the lateral and longitudinal directions as measured by having a Crotch Holding Force (CHF-4.0) of greater than about 0.1 kgf and a Crotch Holding Force (CHF-2.0) of less than about 1.0 kgf;
3) a rear region attached to the front and crotch regions and cooperating with the front region to provide an adjustable waistband; and
4) side elastics in the crotch region, said side elastics having an Elastic Holding Force (EHF-4.5) of less than about 1.0 kgf; and b) an absorbent article capable of being held in close bodily contact in the pudendal region by said thong-shaped holder.

18. A system according to claim 17 wherein the crotch region of the holder has a Crotch Holding Force (CHF-2.0) of less than about 0.6 kgf.

19. A system according to claim 17 wherein the crotch region of the holder has a Crotch Holding Force (CHF-4.0) of less than about 1.0 kgf.

20. A system according to claim 19 wherein the side elastics in the crotch region of the holder have an Elastic Holding Force (EHF-4.5) of less than about 0.8 kgf.

* * * * *